United States Patent [19]

Hellstrom et al.

[11] Patent Number: 5,242,824
[45] Date of Patent: Sep. 7, 1993

[54] MONOCLONAL ANTIBODY TO HUMAN CARCINOMAS

[75] Inventors: Ingegerd Hellstrom; Karl E. Hellstrom, both of Seattle, Wash.

[73] Assignee: Oncogen, Seattle, Wash.

[21] Appl. No.: 443,696

[22] Filed: Nov. 29, 1989

Related U.S. Application Data

[63] Continuation-in-part of Ser. No. 289,635, Dec. 22, 1988, abandoned.

[51] Int. Cl.⁵ .................. C12N 5/12; C07K 15/28
[52] U.S. Cl. ..................... 435/240.27; 530/388.8; 530/391.3; 530/387.1
[58] Field of Search .................. 424/85.8, 85.91, 88; 530/387, 388, 388.8, 391.3, 387.1; 435/7, 172.2, 240.27

[56] References Cited

U.S. PATENT DOCUMENTS

| | | | |
|---|---|---|---|
| 4,474,893 | 10/1984 | Reading | 530/387.3 |
| 4,507,391 | 3/1985 | Pukel et al. | 435/7.21 |
| 4,579,827 | 4/1986 | Sakamoto | 435/172.2 |
| 4,612,282 | 9/1986 | Schlom et al. | 435/7.23 |
| 4,613,576 | 9/1986 | Cote et al. | 435/7.21 |
| 4,618,577 | 10/1986 | Handley et al. | 435/7.23 |
| 4,676,980 | 6/1987 | Segal | 424/85.91 |
| 4,683,200 | 7/1987 | Hirohashi et al. | 435/70.21 |
| 4,693,966 | 9/1987 | Houghton et al. | 192/56 R |
| 4,693,971 | 2/1987 | Fradet et al. | 435/17 |
| 4,708,930 | 11/1987 | Kortright et al. | 435/7.23 |
| 4,713,351 | 12/1987 | Knauf | 436/542 |
| 4,713,352 | 12/1987 | Bander et al. | 435/7.23 |
| 4,737,579 | 4/1988 | Hellstrom et al. | 379/82 |
| 4,753,894 | 6/1988 | Frankel | 435/7.23 |
| 4,782,015 | 11/1988 | Allison et al. | 435/7.23 |
| 4,886,745 | 12/1989 | Morhenn | 435/7.23 |

FOREIGN PATENT DOCUMENTS

| | | |
|---|---|---|
| 0157613 | 10/1985 | European Pat. Off. . |
| 0162825 | 11/1985 | European Pat. Off. . |
| 0173648 | 3/1986 | European Pat. Off. . |
| 0190033 | 8/1986 | European Pat. Off. . |
| 0212403 | 3/1987 | European Pat. Off. . |
| 0218257 | 4/1987 | European Pat. Off. . |
| 0272113 | 6/1988 | European Pat. Off. . |
| 8704183 | 7/1987 | World Int. Prop. O. . |

OTHER PUBLICATIONS

Blaszczth et al. *Journal of Biological Chemistry* vol. 262 No. 1 Issue Jan. 5, 1987 p. 372.
Brown et al. *Bio. Sci. Rep.* 1983; 3 163–170 (Abstract).
Nudelman et al., *Journal of Biological Chemistry* vol. 26 No. 24 1986, 11247.
Sears, *Lancet* (Apr. 1982) 762–765.
Herlyn, *PNAS* (1979) 76(3) 1438–1442.
Canelios, et al., "Autologous Bone Marrow Transplantation in the Treatment of Malignant Lymphoma and Hodgkins Disease," *Seminars in Hematology* 25, Supp. 2, 58–65 (1988).
Liu, et al., "Kimeric House–Human IgG 1 Antibody That Can Mediate Lysis of Cancer Cells," *Proc. Natl. Acad. Sci. USA* 84, 3439–3443 (1987).

(List continued on next page.)

Primary Examiner—David L. Lacey
Assistant Examiner—Lila Feisee
Attorney, Agent, or Firm—Pennie & Edmonds

[57] ABSTRACT

The present invention relates to a novel monoclonal antibody reactive with human carcinoma cells. More particularly, the antibody of the invention is a monoclonal antibody reactive with a glycolipid cell membrane antigen on the surface of human carcinomas. The antibody displays a high degree of selectivity for carcinoma cells, showing a low degree of reactivity with certain normal human cells and no detectable reactivity with other types of tumors such as lymphomas, sarcomas or melanomas. In addition, the antibody of the invention is capable of internalizing within the carcinoma cells to which it binds and is therefore particularly useful for therapeutic applications, for example, as the antibody component of antibody-drug or antibody-toxin conjugates.

8 Claims, 11 Drawing Sheets

OTHER PUBLICATIONS

Bregni, et al., "Elimination of Clonogenic Tumor Cells from Human Bone Marrow Using a Combination of Monoclonal Antibody: Ricin A-Chain Conjugates," *Cancer Res.* 46, 1208-1213 (1986).

Yang, et al., "Human Transferrin cDNA characterization in Chromosomal Location," *Proc. Natl. Acad. Sci. USA* 81, 2752-2756 (1984).

Trowbridge, et al., "Monoclonal Antibodies to Transferrin Receptor and Assay of Their Biological Effects," *Meth. Enzymol.* 265-279 (1987).

Trowbridge, et al., "Murine Cell Surface Transferrin Receptor: Studies with an Anti-receptor Monoclonal Antibody," *J. Cell Physiol.* 112, 403-410 (1982).

Trowbridge, I. S., Lopez, F., "Monoclonal Antibody to Transferrin Receptor Blocks Transferrin Binding and Inhibits Tumor Cell Growth in vitro," *Proc. Natl. Acad. Sci. USA* 79, 1175-1179 (1982).

Hopkins, C. R., Trowbridge, I. S., "Internalization and Processing of Transferrin and the Transferrin Receptor in Human Carcinoma A431 Cells," *J. Cell Biol.* 97, 508-521 (1983).

Borrebaeck, et al., "Human Monoclonal Antibodies Produced by Primary in vitro Immunization of Peripheral Blood Lymphocytes," *Proc. Natl. Acad. Sci. USA* 85, 3995-3999 (1988).

Urdal, D. L. Hakomori, S., "Tumor-associated Ganglio-N-Triosylceramide," *J. Biol. Chem.* 235, 10509-16 (1980).

Hellstrom, K. E., Hellstrom, I., "Anti-melanoma Antibodies for Therapy," in *Human Melanoma* (S. Ferrone, Ed. Springer-Verlag), pp. 1-58.

Papsidero, "Recent Progress in the Immunological Monitoring of Carcinomas Using Monoclonal Antibodies", *Semin. Surg. Oncol.,* 1 (No. 4), pp. 171-81 (1985).

Schlom et al., "Potential Clinical Utility of Monoclonal Antibodies in the Management of Human Carcinomas", *Important Adv. Oncol.*, pp. 170-192 1985.

Allum, et al., "Monoclonal Antibodies in the Diagnosis and Treatment of Malignant Conditions", *Surg. Ann.,* 18, pp. 41-64 (1986).

Houghton, et al., "Monoclonal Antibodies: Potential Applications to the Treatment of Cancer", *Semin. Oncol.,* 13 (No. 2), pp. 165-179 (1986).

Fink, et al., "Monoclonal Antibodies as Diagnostic Reagents for the Identification and Characterization of Human Tumor Antigens", *Prog. Clin. Pathol.* 9, pp. 121-133 (1984).

Johnston, "Applications of Monoclonal Antibodies in Clinical Cytology as Exemplified by Studies with Monoclonal Antibody B72.3", *Acta. Cytol.,* 1 (No. 5), pp. 537-556 (1987).

Young, et al., "Production of Monoclonal Antibodies Specific for Two Distinct Steric Portions of the Glycolipid Ganglio-N-Triosylceramide (Asialo $GM_2$)", *J. Exp. Med.,* 150, pp. 1008-1019 (1979).

Kniep, et al., "Gangliotriaosylceramide (Asialo $GM_2$) A Glycosphingolipid Marker for Cell Lines Derived from Patients With Hodgkin's Disease", *J. Immunol.,* (No. 3), pp. 1591-1594 (1983).

Rosen, et al., "Analysis of Human Small Cell Lung Cancer Differentiation Antigens Using A Panel of Rat Monoclonal Antibodies", *Cancer Research,* 44, pp. 2052-2061 (1984).

Varki, et al., "Antigens Associates With a Human Lung Adenocarcinoma Defined By Monoclonal Antibodies", *Cancer Research,* 44, pp. 681-687 (1984).

Hellstrom, et al., "Antitumor Effects of L6, An IgG2a Antibody that Reacts With Most Human Carcinomas", *Proc. Natl. Acad. Sci. USA,* 83, pp. 7059-7063 (1986).

Embleton, et al., "Antibody Targeting of Anti-Cancer Agents", in *Monoclonal Antibodies for Cancer Detection and Therapy,* pp. 317-344 (Academic Press) (1985).

Domingo, et al., "Transferrin Receptor as a Target for Antibody-Drug Conjugates", *Methods Enzymol.* 112, pp. 238-247 (1985).

Hakomori, "Tumor-Associated Carbohydrate Antigens", *Ann. Rev. Immunol.* 2: 103-126 (1984).

Hellstrom, et al., "Monoclonal Mouse Antibodies Raised Against Human Lung Carcinoma", *Cancer Res.,* 46, pp. 3917-3923 (1986).

Magnani, et al., "Mouse and Rat Monoclonal Antibodies Directed Against Carbohydrates", in *Methods Enzymol.,* 138, pp. 484-491 (1987).

(List continued on next page.)

OTHER PUBLICATIONS

Novel Effector Functions" *Nature*, 312 pp. 604–608 (1984).

Ul, et al., "Chimeric Antibodies", *Biotechniques*,4 (No. 3), pp. 214–221 (1986).

Nudelman, et al., "Characterization of A Human Melanoma-Associated Ganglioside Antigen Defined by a Monoclonal Antibody 4 2", *J. Biol. Chem.*, 257 (No. 1), pp. 12752–12756 (1982).

Nepom, et al., "Anti-Idiotypic Antibodies and the Induction of Specific Tumor Immunity", in *Cancer and Metastasis Reviews*, 6, pp. 487–501 (1987).

Ciocca, et al., "Immunohistochemical Techniques Using Monoclonal Antibodies", *Meth. Enzymol., 121, pp. 562–579 (1986).*

Kimball, *Introduction to Immunology*, pp. 113–117 (1987).

Uotila, et al., "Two-Site Sandwich ELISA With Monoclonal Antibodies to Human AFP", *J. Immunol Methods*, 42, p. 11 (1981).

Sikora, et al., *Monoclonal Antibodies*, pp. 32–52 (Blackwell Scientific Publications) (1984).

Wensel and Meares, *Radioimmunoimaging and Radioimmunotherapy*, Esevier, New York (1983).

Colcher, et al., "Use of Monoclonal Antibodies As Radiopharmaceuticals For The Localization of Human Carcinoma Xenografts in Athymic Mice", *Meth. Enzymol.*, 802–16 (1986).

Bradwell, et al., "Developments in Antibody Imaging", in *Monoclonal Antibodies For Cancer Detection and Therapy*, R. W. Baldwin et al. (eds.), pp. 65–85 (Academic Press) (1985).

Arnon, et al., "Monoclonal Antibodies For Immunotargeting of Drugs In Cancer Therapy", in *Monoclonal Antibodies And Cancer Therapy*, R. A. Reisfeld et al. (eds.), pp. 243–256 (Alan R. Liss, Inc.) (1985).

Hellstrom, et al., "Antibodies For Drug Delivery", in *Controlled Drug Delivery* (2nd Ed.), J. R. Robinson et al. (eds), pp. 623–653 (Marcel Dekker, Inc.) (1987).

Thorpe, "Antibody Carriers of Cytotoxic Agents In Cancer Therapy.: A Review", in *Monoclonal Antibodies '84: Biological and Clinical Applications*, A. Pincera et al. (eds.), pp. 475–506 (1985).

Thorpe, et al., "The Preparation and Cytotoxice Properties of Antibody-Toxin Conjugates", *Immunol. Rev.*, 62, pp. 119–158 (1982).

Order, "Analysis, Results, and Future Prospective of the Therapeutic Use of Radiolabeled Antibody", in *Cancer Therapy*, R. W. Baldwin et al. (eds.), pp. 203–216 (Academic Press) (1985).

Kohler, M., Milstein, C., "Continuous Cultures of Fused Cells Secreting Antibody of Pre-Defined Specificity", *Nature*, 256, pp. 495–497 (1975).

Brown, et al., "Structural Characterization of Human Melanoma-Associated Antigen p97 With Monoclonal Antibodies", *J. Immunol.*, 127 (No. 2), pp. 539–546 (1981).

Brown, et al., "Protein Antigens of Normal and Malignant Human Cells Identified by Immunoprecipitation with Monoclonal Antibodies", *J. Biol. Chem.*, 255, pp. 4980–4983 (1980).

Yeh, et al., "Cell Surface Antigens of Human Melanoma Identified By Monoclonal Antibody", *Proc. Natl. Acad. Sci. USA*, 76 (No. 6), pp. 2927–2931 (1979).

Yeh, et al., "A Cell-Surface Antigen which is Present in the Ganglioside Fraction and Shared by Human Melanomae", *Int. J. Cancer*, 29, pp. 269–275 (1982).

Hellstrom, et al., "Immunologic Approaches to Tumor Therapy, Monoclonal Antibodies, Tumor Vaccines, and Anti-Idiotypes", in *Covalently Modified Antigens and Antibodies in Diagnosis and Therapy*, Quash/Rodwell (eds), pp. 24–28 (Marcel Dekker, Inc., in press).

Bagshawe, "Tumor Markers—Where Do We Go From Here", *Br. J. Cancer*, 48 pp. 167–175 (1983).

Rousseaux, et al., "Optimal Conditions For The Preparation of Proteolytic Fragments From Monoclonal IgG of Different Rat IgG Subclasses", in *Methods Enzymol.*, 121, pp. 663–669 (Academic Press 1986).

Thammana, et al., "Immunoglobulin Heavy Chain Class Switch From IgM to IgG in a Hybridoma", *Eur. J. Immunol.*, 13, p. 614 (1983).

Spira et al., "The Identification of Monoclonal Class Switch Variants By Subselection and ELISA Assay", *J. Immunol. Meth.*, 74, pp. 307 15 (1984).

Neuberger, et al., "Recombinant Antibodies Possessing (List continued on next page.)

OTHER PUBLICATIONS

Senter, et al., "Anti-Tumor Effects of Antibody-Alkaline Phosphatase Conjugates In Combination With Etoposide Phosphate", *Proc. Natl. Acad. Sci. USA*, 85, pp. 4842–4846 (1988).

Ramsay, et al., "Bone Marrow Purging Using Monoclonal Antibodies", *J. Clin. Immunol.*, 8 (No. 2), pp. 81–88 (1988).

Douillard, et al., "Enzyme-Linked Immunosorbent Assay for Screening Monoclonal Antibody Production Using Enzyme-Labeled Second Antibody", *Meth. Enzymol.*, 92, pp. 168–174 (1983).

Sternberger, *Immunochemistry*, pp. 104–169 (John Wiley & Sons, New York) (1979).

Carrigues, et al., "Detection of A Human Melanoma-Associated Antigen, p. 97, In Histological Sections of Primary Human Melanoma", *Int. J. Cancer*, 29, pp. 511–515 (1982).

Hellstrom, et al., *J. Immunol., 127, pp. 157–160 (1981)*.

Brown, et al., "Quantitative Analysis of Melanoma-Associated Antigen, p. 97, In Normal and Neoplastic Tissues", *Proc. Natl. Acad. Sci. USA*, 78, 539–543 (1981).

Blakey, et al., *Cancer Res.*, 47, pp. 947–952 (1987).

Lambert, et al., *J. Biol. Chem.*, 260, pp. 12035–12041 (1985).

Knowles, et al., *Anal. Biochem.*, 160, pp. 440–443 (1987).

Yeh, et al., *J. Immunol., 126 (No. 4), pp. 1312–1317 (1981)*.

Shen, et al., *Biochem. Biophys. Res. Commun.*, 102, pp. 1048–1054 (1981).

Yang, et al., *Proc. Natl. Acad. Sci. USA*, 85, pp. 1189–1193 (1988).

Hellstrom, et al., *Proc. Natl. Acad. Sci. (USA)*, 82, pp. 1499–1502 (1985).

Cerrotini et al., *Adv. Immunol.*, 18, 67–132 (1974).

Hellstrom, et al., *Int. J. Cancer* 27, 281–85 (1981).

Hellstrom, et al., Monoclonal Antibodies and Cancer Therapy, *UCLA Symposium on Molecular and Cellular Biology*, New Series, Reisfeld and Sell, (eds.), Liss, NY, 27, pp. 149–164 (1985).

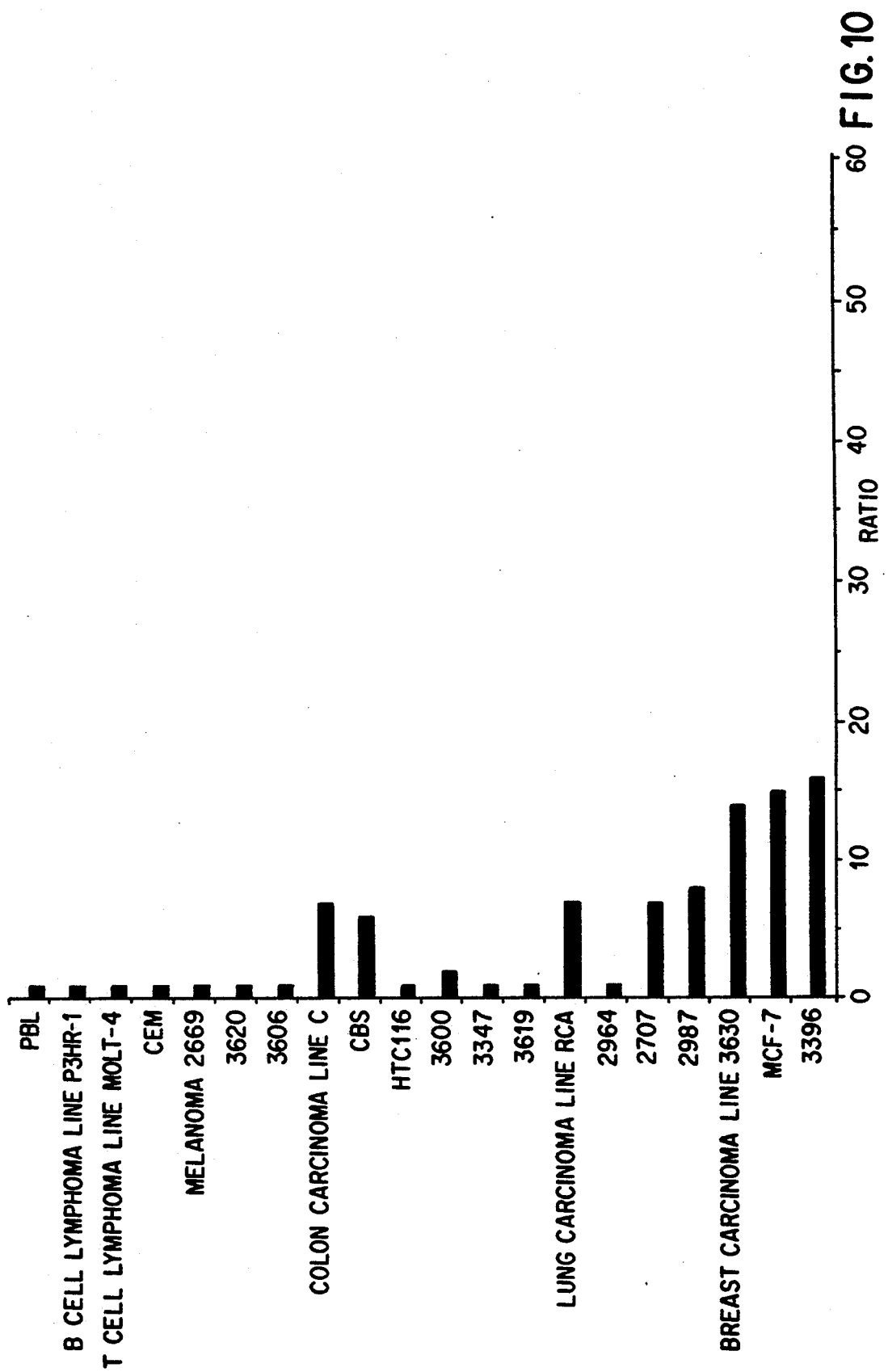

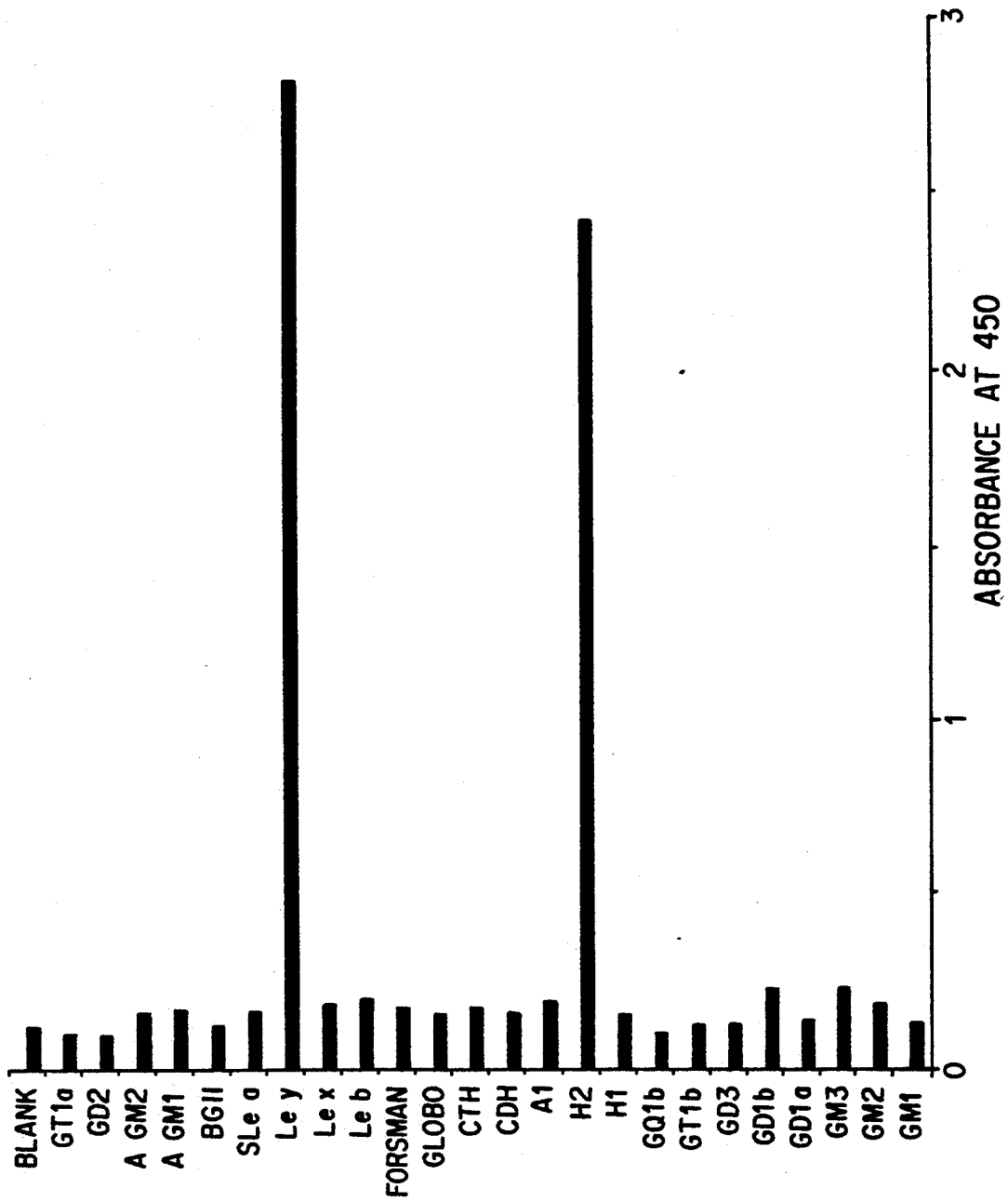

MONOCLONAL ANTIBODY TO HUMAN CARCINOMAS

This application is a continuation-in-part of United States patent application, Ser. No. 289,635, filed on Dec. 22, 1988 in the United States Patent and Trademark Office, now abandoned, which application is incorporated by reference herein in its entirety.

TECHNICAL FIELD OF THE INVENTION

The present invention relates to a novel monoclonal antibody reactive with human carcinoma cells. More particularly, the antibody of the invention is a monoclonal antibody that reacts with a glycolipid cell membrane antigen found on the surface of human carcinomas, such as carcinomas of the colon, breast, ovary, and lung. The antibody is highly specific for carcinoma cells, showing a low degree of reactivity with certain normal human cells and no detectable reactivity with other types of tumors, such as lymphomas, sarcomas or melanomas. The antibody has the added advantage of internalizing within the carcinoma cells to which it binds. The antibody of this invention is, therefore, particularly useful for therapeutic applications, for example, as the antibody component of antibody-drug or antibody-toxin conjugates where internalization of the conjugate is desired. The antibody is also useful in diagnostic methods, such as the detection of malignant carcinomas.

BACKGROUND OF THE INVENTION

Monoclonal antibodies reactive with carcinoma-associated antigens are known [see, e.g., L. D. Papsidero, "Recent Progress in the Immunological Monitoring of Carcinomas Using Monoclonal Antibodies, *Semin. Surg. Oncol.*, 1 (No. 4), pp. 171–81 (1985); J. Schlom et al., "Potential of Human Carcinomas", *Important Adv. Oncol.*, 1985, pp. 170–192; W. H. Allum et al., "Monoclonal Antibodies in the Diagnosis and Treatment of Malignant Conditions", *Surg. Ann.*, 18, pp. 41–64 (1986); and A. N. Houghton et al., "Monoclonal Antibodies: Potential Applications to the Treatment of Cancer", *Semin. Oncol.*, 13 (No. 2), pp. 165–179 (1986)].

These known monoclonal antibodies are principally reactive with specific types of human carcinomas derived from specific organs of the body, e.g., lung, breast, ovarian, colon or other gastrointestinal carcinomas, and can bind to carcinoma-associated antigens that are either glycoprotein or glycolipid in nature [see, e.g., L. M. Fink et al., "Monoclonal Antibodies as Diagnostic Reagents for the Identification and Characterization of Human Tumor Antigens", *Prog. Clin. Pathol.*, 9, pp. 121–133 (1984)]. For example, monoclonal antibodies that bind to glycoprotein antigens on specific types of carcinomas include those described in U.S. Pat. No. 4,737,579 (monoclonal antibodies to non-small cell lung carcinomas), U.S. Pat. No. 4,753,894 (monoclonal antibodies to human breast cancer), U.S. Pat. No. 4,579,827 (monoclonal antibodies to human gastrointestinal cancer), and U.S. Pat. No. 4,713,352 (monoclonal antibodies to human renal carcinoma). Monoclonal antibody B72.3, however, appears to recognize a tumor-associated oncofetal glycoprotein antigen of greater than 1,000 kd molecular weight that is selectively expressed on a number of different carcinomas. Thus, B72.3 has been shown to react with 84% of breast carcinomas, 94% of colon carcinomas, 100% of ovarian carcinomas, and 96% of non-small-cell lung carcinomas [see W. W. Johnston, "Applications of Monoclonal Antibodies in Clinical Cytology as Exemplified by Studies with Monoclonal Antibody B72.3", *Acta Cytol.*, 1 (No. 5), pp. 537–556 (1987), and U.S. Pat. No. 4,612,282, issued to Schlom et al.]. Similarly, monoclonal antibody KC-4 recognizes an approximately 400–500 kd protein antigen expressed on a number of carcinomas, such as colon, prostate, lung, and breast carcinoma [see U.S. Pat. No. 4,708,930]. It appears that neither the B72.3 nor KC-4 antibodies internalize within the carcinoma cells with which they react.

Monoclonal antibodies reactive with glycolipid antigens that are believed to be associated with certain tumor cells have also been disclosed. For example, W. W. Young et al., "Production of Monoclonal Antibodies Specific for Two Distinct Steric Portions of the Glycolipid Ganglio-N-Triosylceramide (Asialo $GM_2$)", *J. Exp. Med.*, 150, pp. 1008–1019 (1979) disclose the production of two monoclonal antibodies specific for asialo GMhd, a cell surface glycosphingolipid antigen that was established as a marker for BALB/c3T3 cells transformed by Kirsten murine sarcoma virus. See, also, B. Kniep et al., "Gangliotriaosylceramide (Asialo $GM_2$), A Glycosphingolipid Marker for Cell Lines Derived from Patients with Hodgkin's Disease", *J. Immunol.*, 131 (No. 3), pp. 1591–1594 (1983), and U.S. Pat. No. 4,507,391 (monoclonal antibody to human melanoma).

In addition, monoclonal antibodies reactive with glycolipid antigens found on specific types of carcinoma cells include those described by S. T. Rosen et al., "Analysis of Human Small Cell Lung Cancer Differentiation Antigens Using a Panel of Rat Monoclonal Antibodies", *Cancer Research*, 44, pp. 2052–2061 (1984), (monoclonal antibodies to human small cell lung cancer), N. M. Varki et al., "Antigens Associated with a Human Lung Adenocarcinoma Defined by Monoclonal Antibodies", *Cancer Research*, 44, pp. 681–687 (1984), (monoclonal antibodies to human adenocarcinomas of the lung, stomach and colon, and melanoma), and U.S. Pat. No. 4,579,827 (monoclonal antibodies to human colon adenocarcinoma). See, also, I. Hellstrom et al., "Antitumor Effects of L6, An IgG2a Antibody that Reacts with Most Human Carcinomas", *Proc. Natl Acad. Sci. USA*, 83, pp. 7059–7063 (1986) which describes the L6 monoclonal antibody that recognizes a carbohydrate antigen expressed on the surface of human non-small cell lung carcinomas, breast carcinomas, and colon carcinomas. The antigen with which the L6 antibody reacts is one that does not internalize within the carcinoma cell.

Other monoclonal antibodies exhibiting a reactivity to carcinoma cells are greatly needed. This is so because of the antigenic heterogeneity of many carcinoma tumors which often necessitates, in diagnosis or therapy, the use of a number of different monoclonal antibodies to the same tumor mass. Furthermore, monoclonal antibodies that display a high degree of selectivity to a wide range of carcinoma tissues are not common, and any such antibody would clearly be advantageous.

Of particular interest, especially in the area of therapeutic applications for monoclonal antibodies, would be so called "internalizing" antibodies, i.e., antibodies that are capable of being internalized within the tumor cell to which they bind. This type of antibody finds use in tumor therapy methods involving antibody-drug or antibody-toxin conjugates wherein a therapeutic antitumor agent is linked to an antibody for delivery to the site of a tumor, where the antibody binds to the tumor-associated antigen with which it is reactive and "delivers" the antitumor agent to the tumor site [see, e.g., M. J. Embleton et al., "Antibody Targeting of Anti-Cancer Agents", in *Monoclonal Antibodies for Cancer Detection and Therapy*, pp. 317-344 (Academic Press 1985)]. Because many antibodies to tumor-associated antigens are not able to internalize within the tumor cell to which they bind, often the antitumor agent is not able to reach its site of action within the cell. The use of an internalizing antibody as a component of the conjugate is believed to promote the antitumor activity of such a conjugate.

An example of an internalizing antibody is the anti-transferrin receptor antibody disclosed in D. L. Domingo et al., "Transferrin Receptor as a Target for Antibody-Drug Conjugates", *Methods Enzymol.*, 112, pp. 238-247 (1985). This antibody is reactive with the human transferrin-receptor glycoprotein expressed on tumor cells. However, because the transferrin-receptor glycoprotein is also expressed on normal tissues, the use of an anti-transferrin-receptor antibody in a antibody-drug or antibody-toxin conjugate may have significant toxic effects on normal cells. The utility of this antibody for selective killing or inhibition of tumor cells is therefore questionable.

It is thus apparent that an antibody reactive with a carcinoma-associated antigen that is capable of being readily internalized by tumor cells and also displays a high degree of selectivity to a range of carcinoma cell types would be of great benefit in tumor therapy.

SUMMARY OF THE INVENTION

The present invention provides such an internalizing antibody that is highly selective for a range of human carcinomas. More specifically, the novel antibody of the invention, illustrated by BR64, is a monoclonal antibody that binds to a glycolipid cell membrane antigen found on the surface of human carcinoma cells. The antibody is highly specific for carcinoma cells, such as those derived from breast, lung, colon, and ovarian carcinomas, showing only a low degree of reactivity with certain normal human cells and no detectable reactivity with other types of tumors, such as lymphomas, sarcomas or melanomas. In addition, the antibody of the invention internalizes within the carcinoma cells to which it binds and thus is of particular use for therapeutic applications, for example, as the antibody component of antibody-drug and antibody-toxin conjugates where internalization of the conjugate is favored. The antibody is also useful in in vitro or in vivo diagnostic methods for the detection of carcinoma cells.

BRIEF DESCRIPTION OF THE DRAWINGS

FIG. 10 depicts the binding of the BR64 antibody of the invention to various cultured carcinoma cell lines. Peripheral blood leukocytes (PBL) were used as a negative control. A ratio between the brightness (LFE) of cells stained by BR64 vs. a control antibody was determined by FACS.

FIG. 11 is a bar graph depicting the results of an ELISA assay to detect the binding of the BR64 antibody to known glycolipid antigens.

DETAILED DESCRIPTION OF THE INVENTION

Figure 1:
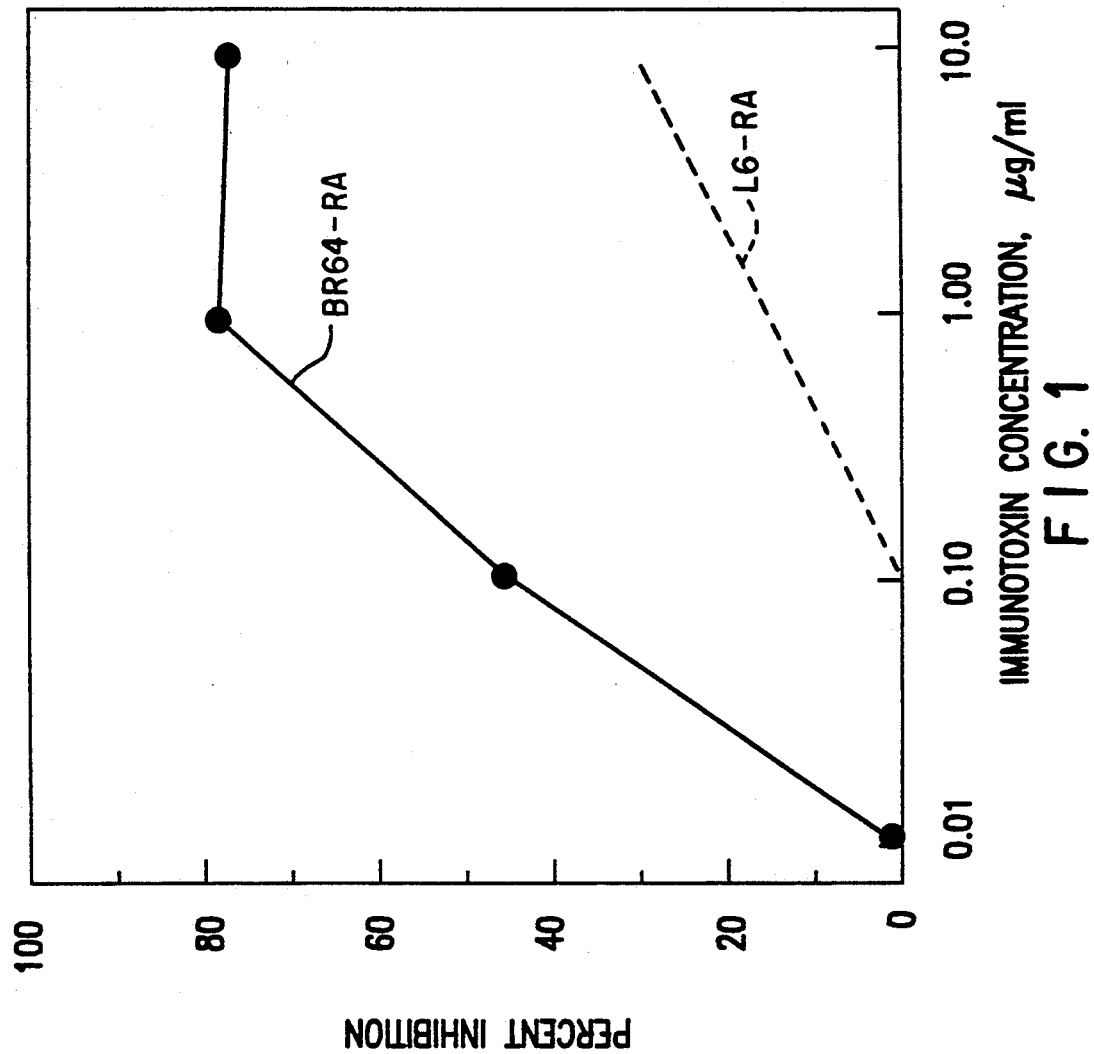
FIG. 1 depicts the percent inhibition of thymidine incorporation into the DNA of H2707 lung carcinoma cells treated with a BR64-RA immunotoxin at varying concentrations. L6-RA is a non-internalizing negative control. This figure demonstrates internalization of the immunotoxin.
Figure 2:
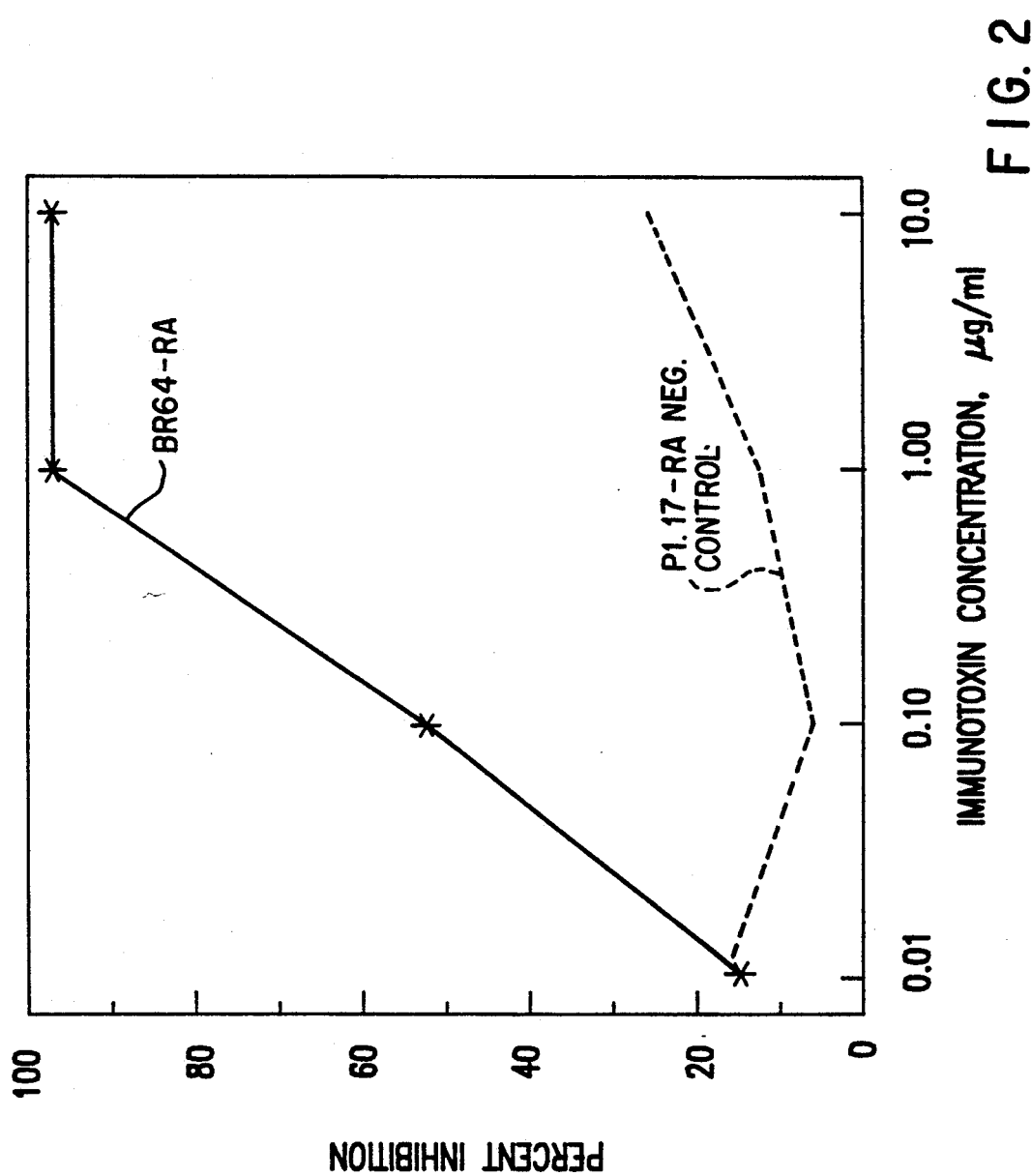
FIG. 2 depicts the percent inhibition of thymidine incorporation into the DNA of H3396 breast carcinoma cells treated with a BR64-RA immunotoxin at varying concentrations. P1.17-RA is a non-internalizing negative control. This figure demonstrates internalization of the immunotoxin.
Figure 3:
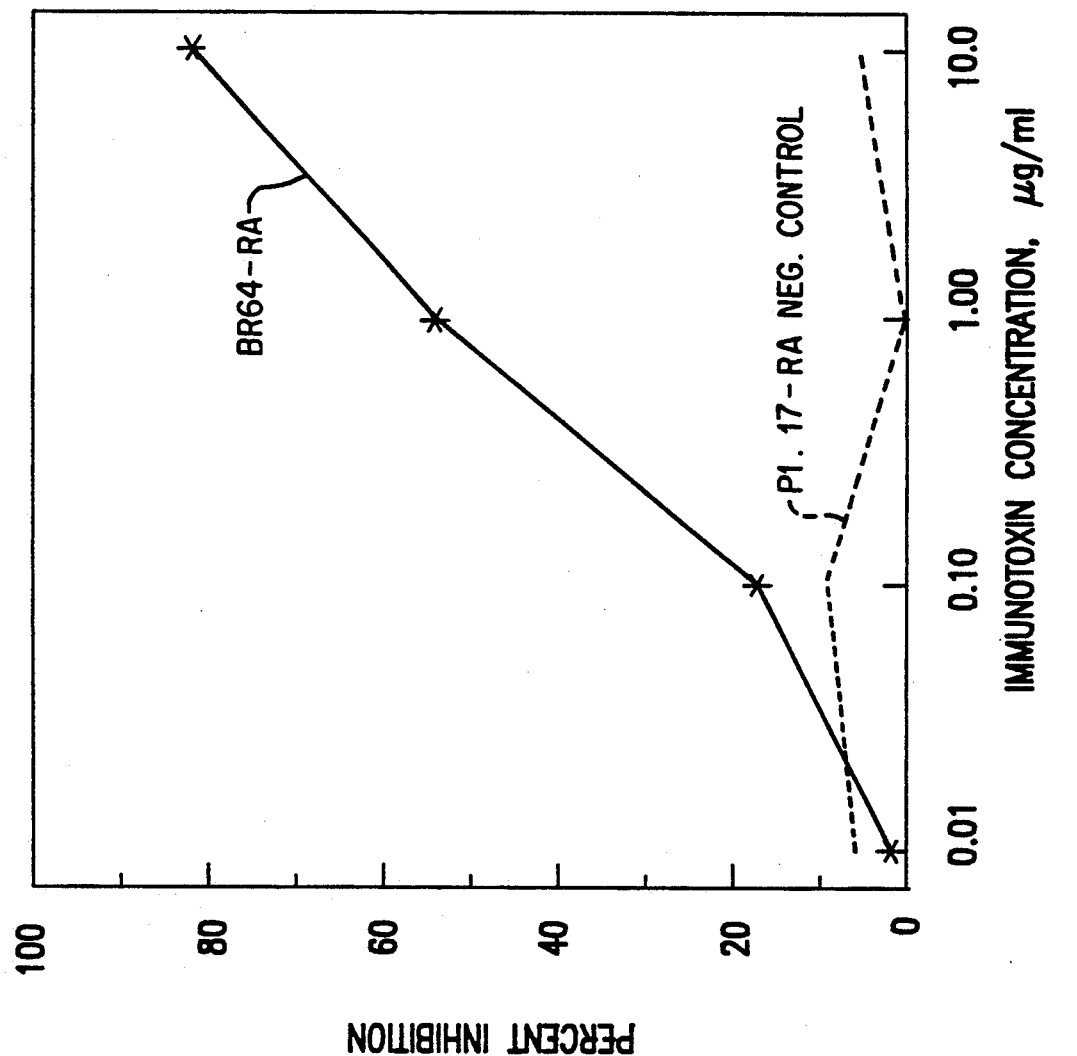
FIG. 3 depicts the percent inhibition of thymidine incorporation into the DNA of C colon carcinoma cells treated with a BR64-RA immunotoxin at varying concentrations. P1.17-RA was used as a negative control. This figure demonstrates internalization of the immunotoxin.
Figure 4:
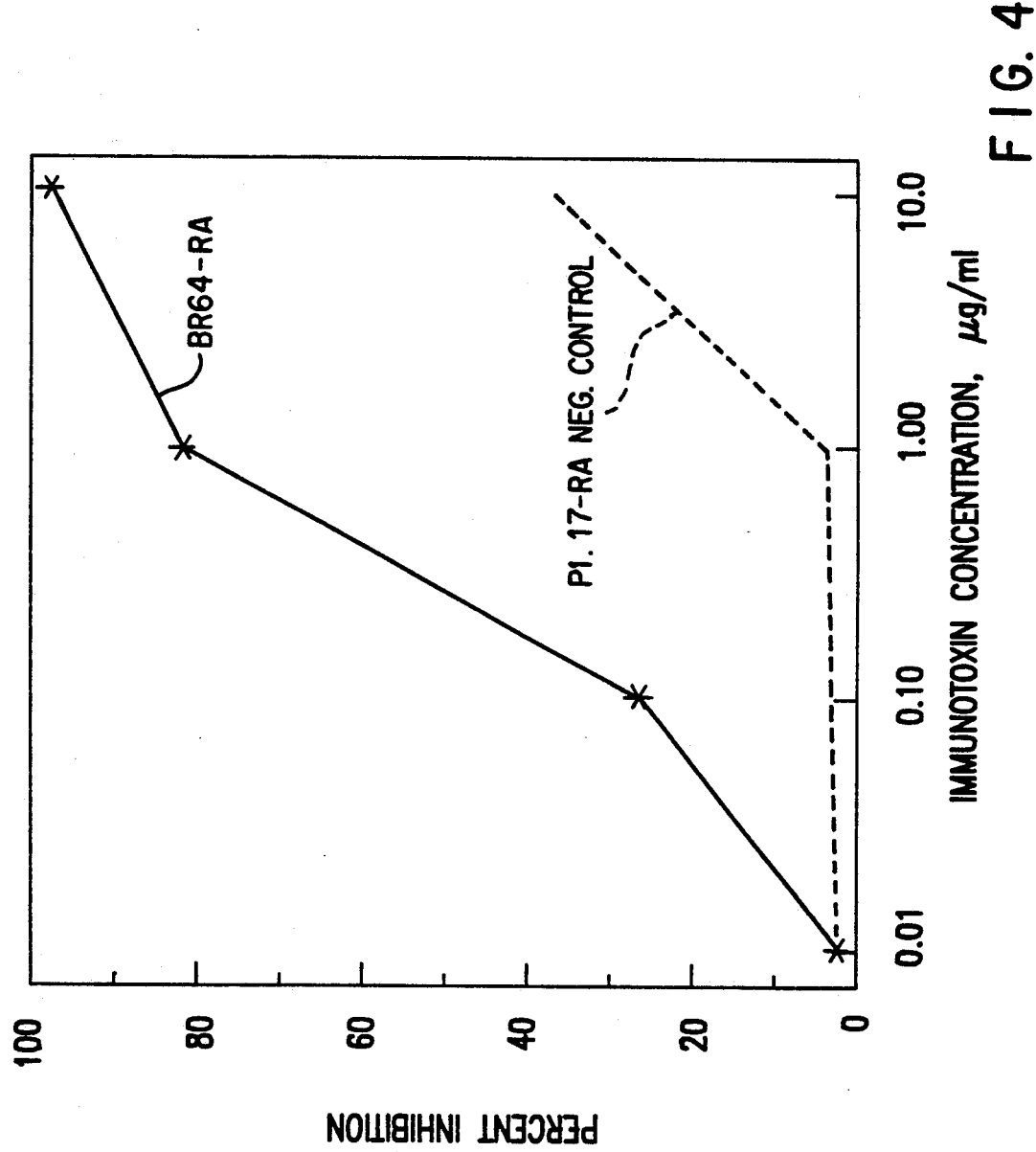
FIG. 4 depicts the percent inhibition of thymidine incorporation into the DNA of RCA colon carcinoma cells treated with a BR64-RA immunotoxin at varying concentrations. P1.17-RA was used as a negative control. This figure demonstrates internalization of the immunotoxin.
Figure 5:
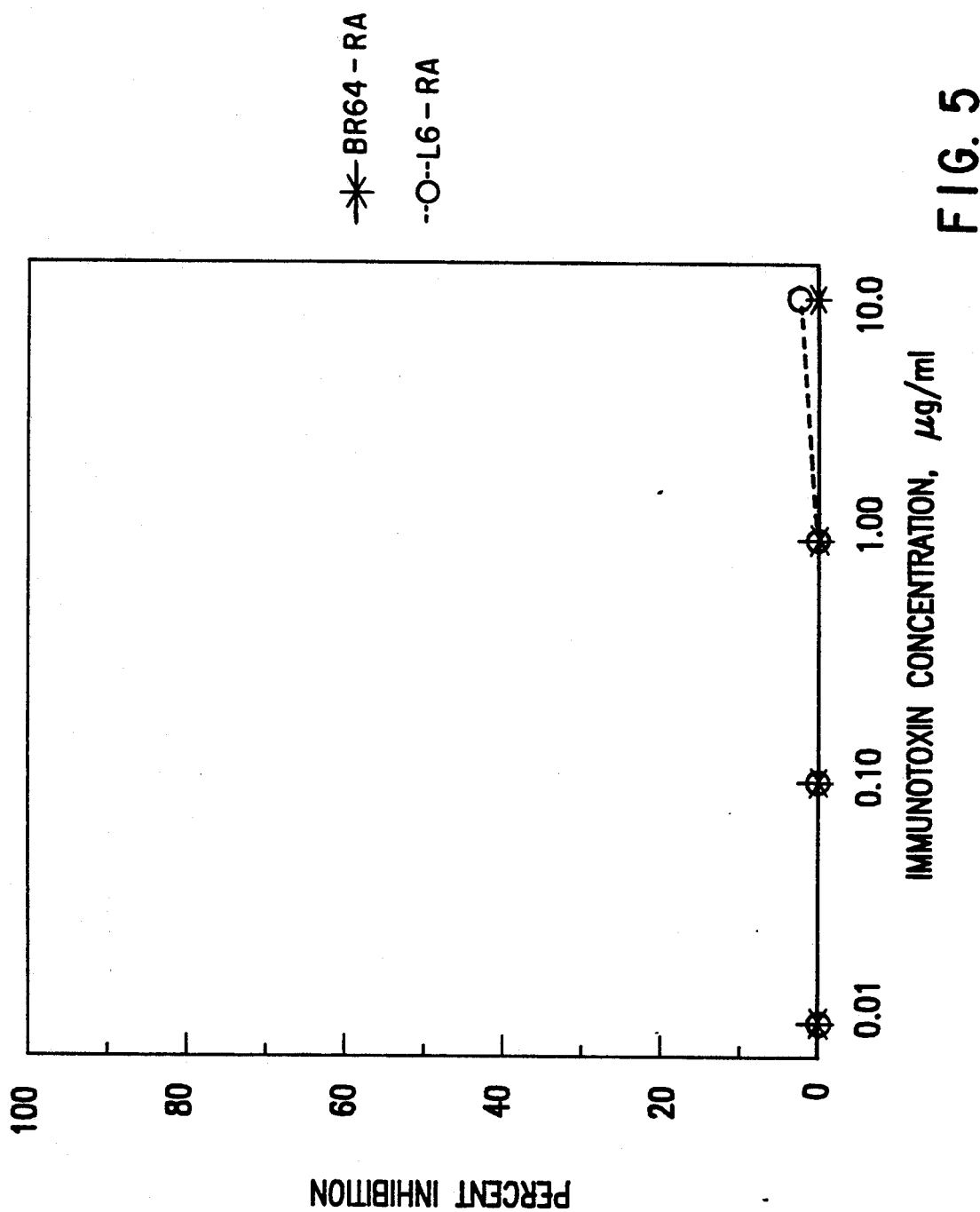
FIG. 5 depicts the percent inhibition of thymidine incorporation into the DNA of JiJoye cells treated with a BR64-RA immunotoxin at varying concentrations. L6-RA is a non-internalizing negative control. No internalization of the immunotoxin occurred.

In order that the invention herein described may be more fully understood, the following detailed description is set forth.

The present invention relates to a novel monoclonal antibody that is highly specific for human carcinoma cells. More particularly, the antibody reacts with a range of carcinomas, such as breast, lung, ovary, and colon carcinomas, while showing a relatively low degree of reactivity with certain normal human tissues and no detectable reactivity with other types of tumors, such as melanomas, sarcomas or lymphomas.

Immunoprecipitation studies with radiolabeled target carcinoma cells and the antibody described herein, followed by preparative sodium dodecylsulfate polyacrylamide electrophoresis (SDS-PAGE), have indicated that the cell membrane antigen on the carcinoma cells to which the antibody binds is not a glycoprotein. Rather, ELISA binding studies with known glycolipid antigens have demonstrated that the antibody binds to a Lewis Y (Le$^y$) carbohydrate antigen [see, e.g., S. Hakomori, "Tumor Associated Carbohydrate Antigens", *Annu. Rev. Immunol.*, 2, pp. 103-126 (1984) and I. Hellstrom et al., "Monoclonal Mouse Antibodies Raised Against Human Lung Carcinoma", *Cancer Res.*, 46, pp. 3917-3923 (1986)], as well as the Le$^y$-related H2 glycolipid antigen [see, e.g., J. L. Magnani, "Mouse And Rat Monoclonal Antibodies Directed Against Carbohydrates", in *Methods Enzymol.*, 138, pp. 484-491 (1987)]. This data, along with other evidence discussed infra, indicates that the antibody of this invention recognizes a complex epitope of a novel pan-carcinomic glycolipid antigen, a portion of that epitope comprising an Le$^y$ carbohydrate chain.

Furthermore, studies using radiolabeled antibody or antibody to which an antitumor agent (e.g., drug or toxin) has been coupled, have shown that the antibody of this invention is one that is readily and rapidly internalized by the carcinoma cells with which it binds.

The monoclonal antibody of the invention can be produced using well-established hybridoma techniques first introduced by Kohler and Milstein [see, M. Kohler and C. Milstein, "Continuous Cultures of Fused Cells Secreting Antibody of Pre-Defined Specificity", *Nature*, 256, pp. 495-497 (1975)]. See, also, J. P. Brown et al., "Structural Characterization of Human Melanoma-Associated Antigen p97 With Monoclonal Antibodies", *J. Immunol.*, 127 (No. 2), pp. 539-546 (1981); J. P. Brown et al., "Protein Antigens of Normal and Malignant Human Cells Identified by Immunoprecipitation with Monoclonal Antibodies", *J. Biol. Chem.*, 255, pp. 4980-4983 (1980); M. Yeh et al., "Cell Surface Antigens of Human Melanoma Identified by Monoclonal Antibody", *Proc. Natl. Acad. Sci. USA*, 76 (No. 6), pp. 2927-2931 (1979); and M. Yeh et al., "A Cell-Surface Antigen which is Present in the Ganglioside Fraction and Shared by Human Melanomas", *Int. J. Cancer*, 29, pp. 269-275 (1982).

These techniques involve the injection of an immunogen (e.g., cells or cellular extracts carrying the antigen or purified antigen) into an animal (e.g., a mouse) so as to elicit a desired immune response (i.e., antibodies) in that animal. After a sufficient time, antibody-producing lymphocytes are obtained from the animal either from the spleen, lymph nodes or peripheral blood. Preferably, the lymphocytes are obtained from the spleen. The splenic lymphocytes are then fused with a myeloma cell line, usually in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/0-Ag14 myeloma lines. These myeloma lines are available from the American Type Culture Collection, Rockville, Md.

Figure 6:
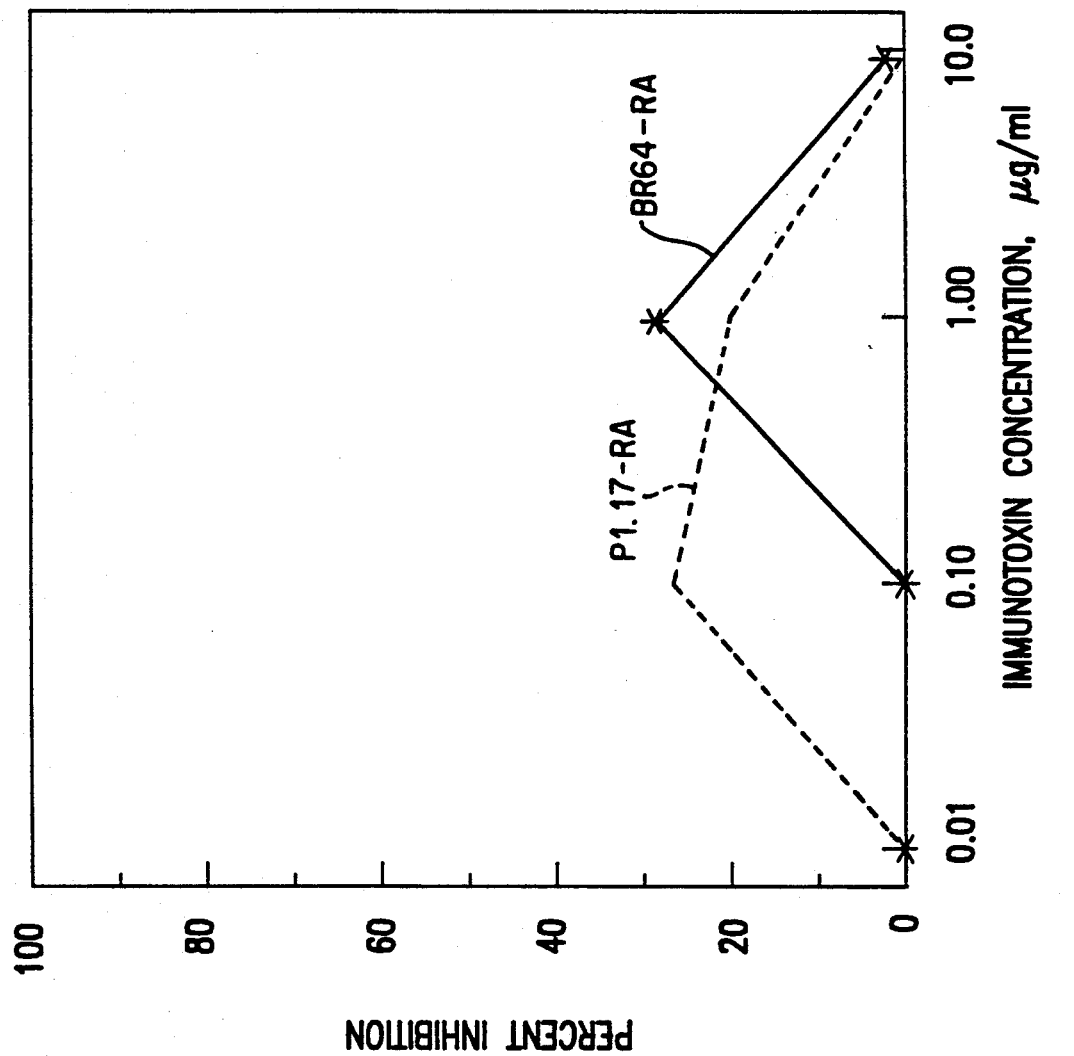
FIG. 6 depicts the percent inhibition of thymidine incorporation into the DNA of normal human fibroblast cells treated with a BR64-RA immunotoxin at varying concentrations. P1.17-RA was used as a negative control. No internalization of the immunotoxin occurred.

The resulting cells, which include the desired hybridomas, are then grown in a selective medium, such as HAT medium, in which unfused parental myeloma or lymphocyte cells eventually die. Only the hybridoma cells survive and can be grown under limiting conditions to obtain isolated clones. The supernatants of the hybridomas are screened for the presence of antibody of that desired specificity, e.g., by immunoassay techniques using the antigen that had been used for immunization. Positive clones can then be subcloned under limiting dilution conditions and the monoclonal antibody produced can be isolated. Hybridomas produced according to these methods can be propagated in vitro or in vivo (in ascites fluid) using techniques known in the art [see, generally, L. M. Fink et al., suprag, p. 123, FIG. 6-1]. Commonly used methods for purifying monoclonal antibodies include ammonium sulfate precipitation, ion exchange chromatography, and affinity chromatography [see, e.g., H. Zola et al., "Techniques for the Production and Characterization of Monoclonal Hybridoma Antibodies", in *Monoclonal Hybridoma Antibodies: Techniques and Applications*, J. G. R. Hurell (ed.), pp. 51-52 (CRC Press 1982)].

According to a preferred embodiment, an antibody of this invention, designated BR64, was produced via the hybridoma techniques described herein below using a breast cancer cell line 3396 as the immunogen. The BR64 hybridoma, prepared as described herein below and producing the BR64 antibody, was deposited on Nov. 3, 1988, with the American Type Culture Collection (ATCC), 12301 Parklawn Drive, Rockville, Maryland, 20852 and has there been identified as follows:

BR64 Accession No.: HB 9895

The BR64 antibody is a murine antibody of the IgG1 subclass. The antibody displays a strong reactivity with a wide range of human carcinoma cells of different organ types, for example, tumors of the breast, lung, colon, stomach, pancreas, and ovary, as well as cell lines from various lung, breast and colon carcinomas. Furthermore, the BR64 antibody shows no detectable binding to other types of tumor cells, such as the T cell lymphoma cell lines, CEM and MOLT-4, the B cell lymphoma cell line P3HR-1, melanoma cells or sarcoma cells.

In addition, the antibody of this invention does not display any immunohistologically detectable binding to most normal human tissues, such as fibroblast, endothelial or epithelial cells from most of the major organs of the body, e.g., kidney, spleen, liver, skin, lung, breast, colon, brain, thyroid, lymph nodes or ovary. Nor does the antibody react with peripheral blood leukocytes or bone marrow stem cells. The antibody does react with certain normal tissues as follows: epithelial cells of the stomach and oesophagus, acinar cells of the pancreas, and occasional cells of the tonsils and testis. Also, in one binding study performed at the NIH, the BR64 antibody appeared to react with cells from salivary glands and Paneth cells in the duodenum. In a separate immunohistological study performed at the NIH, the antibody stained capillaries from three out of six samples of normal heart; however, no such staining was seen with three hearts in studies carried out in the laboratories of the present inventors.

Even taking this low degree of reactivity with certain normal tissues into account, the present antibody is superior to most other known antitumor antibodies in its high degree of specificity for tumor cells as compared to normal cells [see, e.g., K. E. Hellstrom et al., "Immunological Approaches to Tumor Therapy: Monoclonal Antibodies, Tumor Vaccines, and Anti-Idiotypes", in *Covalently Modified Antigens and Antibodies in Diagnosis and Therapy*, Quash/Rodwell (eds.), pp. 24-28 (Marcel Dekker, Inc., in press), and K. D. Bagshawe, "Tumour Markers—Where Do We Go From Here", *Br. J. Cancer*, 48, pp. 167-175 (1983)].

It should be understood that the present invention encompasses the BR64 antibody described above and any fragments thereof containing the active antigen-binding region of the antibody, such as Fab, F(ab')$_2$ and Fv fragments. Such fragments can be produced from the BR64 antibody using techniques well established in the art [see, e.g., J. Rousseaux et al., "Optimal Conditions for the Preparation of Proteolytic Fragments from Monoclonal IgG of Different Rat IgG Subclasses", in *Methods Enzymol.*, 121, pp. 663-669 (Academic Press 1986)].

In addition, the present invention encompasses antibodies that are capable of binding to the same antigenic determinant or epitope as the BR64 antibody and competing with the BR64 antibody for binding at that site. These include antibodies having the same antigenic specificity as the BR64 antibody but differing in species origin, isotype, binding affinity or biological functions (e.g., cytotoxicity). For example, class, isotype and other variants of the antibody of the invention having the antigen-binding region of the BR64 antibody may be constructed using recombinant class-switching and fusion techniques known in the art [see, e.g., P. Thammana et al., "Immunoglobulin Heavy Chain Class Switch from IgM to IgG in a Hybridoma", *Eur. J. Immunol.*, 13, p. 614 (1983); G. Spira et al., "The Identification of Monoclonal Class Switch Variants by Subselection and ELISA Assay, *J. Immunol. Meth.*, 4, pp. 307-315 (1984); M. S. Neuberger et al., "Recombinant Antibodies Possessing Novel Effector Functions", *Nature*, 312, pp. 604-608 (1984); and V. T. Oi et al., "Chimeric Antibodies", *Biotechniques*, 4 (No. 3), pp. 214-221 (1986)]. Thus, chimeric antibodies or other recombinant antibodies (e.g., fusion proteins wherein the antibody is combined with a second protein such as a lymphokine) having the same binding specificity as the BR64 antibody fall within the definition of the antibody of this invention.

Alternatively, variants of the antibody of this invention having the antigen-binding region of the BR64 antibody may be obtained by selection of naturally-occurring class-switch mutants as described by G. Spira et al., "The Identification of Monoclonal Class Switch Variants by Sib Selection and an ELISA Assay", *J. Immunol. Methods*, 74, pp. 307-315 (1984). Such variants also fall within the definition of the antibody of this invention.

According to these methods, an IgG2a variant of BR64, hereinafter referred to as BR64.60, was obtained. The variable region of BR64.60 is the same as that of original BR64 and thus the two antibodies have the same specificity. However, while BR64 sometimes exhibits a weak ADCC (antibody-dependent cellular cytotoxicity), this IgG2a variant possesses significant ADCC, as well as CDC (complement-dependent cytoxicity). The BR64.60 hybridoma that produces the IgG2a variant of BR64 was deposited on Nov. 7, 1989, with the ATCC and has there been identified as follows:

BR64.60 Accession No.: HB 10292

The antibody of this invention can be used to isolate and characterize the antigen to which it binds. Thus, BR64 or BR64.60 can be used as a probe to identify and characterize the epitope recognized by the antibody and to further define the cell membrane antigen with which it reacts [see, e.g., E. Nudelman et al., "Characterization of a Human Melanoma-Associated Ganglioside Antigen Defined by a Monoclonal Antibody, 4.2", *J. Biol. Chem.*, 257 (No. 1), pp. 12752-12756 (1982), and S. Hakomori, "Tumor Associated Carbohydrate Antigens", *Ann. Rev. Immunol.*, 2, pp. 103-126 (1984)].

As stated earlier, studies utilizing the BR64 antibody have indicated that its antigen is not a glycoprotein but rather a glycolipid. Thus, the BR64 antibody was tested for its reactivity to a variety of immobilized glycolipids of known carbohydrate structure in an ELISA assay and was shown to bind to an $Le^y$ [Fuc$\alpha$1-2Gal$\beta$1-4(Fuc$\alpha$1-3)GlcNAc] antigen as well as an H2 [Fuc$\alpha$1-2Gal$\beta$1-4GlcNAc] glycolipid. It should be noted that there are other monoclonal antibodies in the art known to react with $Le^y$ antigens; yet, none of those antibodies have been described as exhibiting the tumor specificity and ability to internalize displayed by the antibody of this invention. Thus, it appears that the present antibody recognizes a complex epitope on a novel pan-carcinomic antigen, a portion of that epitope comprising an $Le^y$ antigen. By the disclosure of the present antibody herein, the present inventors have provided the means with which to obtain this novel antigen. The present invention therefore encompasses antibodies that bind to any antigenic determinant or epitope on this novel antigen, including epitopes other than that with which BR64 reacts.

Also included within the scope of the invention are anti-idiotypic antibodies of the BR64 antibody of the invention. These anti-idiotypic antibodies can be produced using the BR64 antibody as immunogen and are useful for diagnostic purposes in detecting humoral response to tumors and in therapeutic applications, e.g., in a vaccine, to induce an anti-tumor response in patients [see, e.g., G. T. Nepom et al., "Anti-Idiotypic Antibodies and the Induction of Specific Tumor Immunity", in *Cancer and Metastasis Reviews*, 6, pp. 487-501 (1987)].

The monoclonal antibody of the invention is also useful for diagnostic applications, both in vitro and in vivo, for the detection of human carcinomas that possess the antigen for which the antibody is specific. In vitro diagnostic methods include immunohistological detection of tumor cells (e.g., on human tissue, cells or excised tumor specimens) or serologic detection of tumor-associated antigens (e.g., in blood samples or other biological fluids).

Immunohistochemical techniques involve contacting a biological specimen, such as a tissue specimen, with the antibody of the invention and then detecting the presence on the specimen of the antibody complexed to its antigen. The formation of such antibody-antigen complexes with the specimen indicates the presence of carcinoma cells in the tissue. Detection of the antibody on the specimen can be accomplished using techniques known in the art such as immunoenzymatic techniques, e.g., the immunoperoxidase staining technique or the avidin-biotin (ABC) technique, or immunofluorescence techniques [see, e.g., D. R. Ciocca et al., "Immunohistochemical Techniques Using Monoclonal Antibodies", *Meth. Enzymol.*, 121, pp. 562-579 (1986); I. Hellstrom et al., "Monoclonal Mouse Antibodies Raised Against Human Lung Carcinoma", *Cancer Research*, 46, pp. 3917-3923 (1986); and J. W. Kimball (ed.), *Introduction to Immunology* (2nd Ed.), pp. 113-117 (Macmillan Publ. Co. 1986)]. For example, immunoperoxidase staining was used as described in Example 2, infra, to demonstrate the reactivity of the BR64 antibody with lung, breast, colon, and ovary carcinomas and the relative lack of reactivity of the antibody with normal human tissue specimens.

Serologic diagnostic techniques involve the detection and quantitation of tumor-associated antigens that have been secreted or "shed" into the serum or other biological fluids of patients thought to be suffering from carcinoma. Such antigens can be detected in the body fluids using techniques known in the art such as radioimmunoassays (RIA) or enzyme-linked immunosorbent assays (ELISA) wherein an antibody reactive with the "shed" antigen is used to detect the presence of the antigen in a fluid sample [see, e.g., M. Uotila et al., "Two-Site Sandwich ELISA with Monoclonal Antibodies to Human AFP", *J. Immunol. Methods,* 42, p. 11 (1981) and W. H. Allum et al., supra at pp. 48–51]. These assays, using the BR64 antibody disclosed herein, can therefore be used for the detection in biological fluids of the glycolipid antigen with which the BR64 antibody reacts and thus the detection of human carcinoma in patients. Thus, it is apparent from the foregoing that the antibody of the invention can be used in most assays involving antigen-antibody reactions. These assays include, but are not limited to, standard RIA techniques, both liquid and solid phase, as well as ELISA assays procedures, immunofluorescence techniques, and other immunocytochemical assays [see, e.g., K. Sikora et al. (eds.), *Monoclonal Antibodies,* pp. 32–52 (Blackwell Scientific Publications 1984)].

The invention also encompasses diagnostic kits for carrying out the assays described above. In one embodiment, the diagnostic kit comprises the BR64 (or BR64.60) monoclonal antibody and a conjugate comprising a specific binding partner for the antibody and a label capable of producing a detectable signal. The reagents may also include ancillary agents such as buffering agents and protein stabilizing agents (e.g., polysaccharides). The diagnostic kit may further comprise, where necessary, other components of the signal-producing system, including agents for reducing background interference, control reagents or an apparatus or container for conducting the test. In another embodiment, the diagnostic kit comprises a conjugate of the BR64 (or BR64.60) monoclonal antibody of the invention and a label capable of producing a detectable signal. Ancillary agents, as mentioned above, may also be present.

The antibody of the invention is also useful for in vivo diagnostic applications for the detection of human carcinomas. One such approach involves the detection of tumors in vivo by tumor imaging techniques. According to this approach, the antibody or fragments thereof, e.g., Fab or F(ab')$_2$, are labeled with an appropriate imaging reagent that produces a detectable signal. Examples of imaging reagents that can be used include, but are not limited to, radiolabels such as $^{131}$I, $^{111}$In, $^{123}$I, $^{99m}$Tc, $^{32}$P, $^{125}$I, $^{3}$H, and $^{14}$C, fluorescent labels such as fluorescein and rhodamine, and chemiluminescers such as luciferin. The antibody can be labeled with such reagents using techniques known in the art. For example, see Wensel and Meares, *Radioimmunoimaging and Radioimmunotherapy,* Esevier, New York (1983), for techniques relating to the radiolabeling of antibodies [see also, D. Colcher et al., "Use of Monoclonal Antibodies as Radiopharmaceuticals for the Localization of Human Carcinoma Xenografts in Athymic Mice", *Meth. Enzymol.,* 121, pp. 802–816 (1986)].

In the case of radiolabeled antibody, the antibody is administered to the patient, localizes to the tumor bearing the antigen with which the antibody reacts, and is detected or "imaged" in vivo using known techniques such as radionuclear scanning using, e.g., a gamma camera or emission tomography [see, e.g., A. R. Bradwell et al., "Developments in Antibody Imaging", in *Monoclonal Antibodies for Cancer Detection and Therapy,* and R. W. Baldwin et al., (eds.), pp. 65–85 (Academic Press 1985)]. The antibody is administered to the patient in a pharmaceutically acceptable carrier, such as water, saline, Ringer's solution, Hank's solution or nonaqueous carriers such as fixed oils. The carrier may also contain substances that enhance isotonicity and chemical stability of the antibody such as buffers or preservatives. The antibody formulation is administered, for example, intravenously at a dosage sufficient to provide enough gamma emission to allow visualization of the tumor target site. Sufficient time should be allowed between administration of the antibody and detection of an imaging signal to enable the antibody to localize to the tumor target. For a general discussion of tumor imaging, see W. H. Allum et al., supra at pp. 51–55.

The BR64 antibody of the invention has a number of in vivo therapeutic applications. First, the antibody can be used in conjunction with an appropriate therapeutic agent to treat human carcinoma. For example, the antibody can be conjugated or linked to a therapeutic drug or toxin for delivery of the therapeutic agent to the site of the carcinoma. Techniques for conjugating such therapeutic agents to antibodies are well known [see, e.g., R. Arnon et al., "Monoclonal Antibodies for Immunotargeting of Drugs in Cancer Therapy", in *Monoclonal Antibodies and Cancer Therapy*; R. A. Reisfeld et al. (eds.) pp. 243–256 (Alan R. Liss, Inc. 1985); K. E. Hellstrom et al., "Antibodies for Drug Delivery", in *Controlled Drug Delivery,* (2nd Ed.); J. R. Robinson et al. (eds.), pp. 623–653 (Marcel Dekker, Inc. 1987); P. E. Thorpe, "Antibody Carriers of Cytotoxic Agents in Cancer Therapy: A Review", in *Monoclonal Antibodies '84: Biological and Clinical Applications*; A. Pinchera et al. (eds.), pp. 475–506 (1985); and P. E. Thorpe et al., "The Preparation and Cytotoxic Properties of Antibody-Toxin Conjugates", Immunol. Rev., 62, pp. 119–158 (1982)]. The BR64 antibody of the invention is particularly suited for use in a therapeutic conjugate because it is readily internalized within the carcinoma cells to which it binds and so can deliver the therapeutic agent to intracellular sites of action.

Alternatively, the antibody can be coupled to high-energy radiation, e.g., a radioisotope such as $^{131}$I, which, when localized at the tumor site, results in a killing of several cell diameters [see, e.g., S. E. Order, "Analysis, Results, and Future Prospective of the Therapeutic Use of Radiolabeled Antibody in Cancer Therapy", in *Monoclonal Antibodies for Cancer Detection and Therapy,* and R. W. Baldwin et al. (eds.), pp. 303–316 (Academic Press 1985)]. According to yet another embodiment, the BR64 can be conjugated to a second antibody to form an antibody heteroconjugate for the treatment of tumor cells as described by D. M. Segal in U.S. Pat. No. 4,676,980.

Still other therapeutic applications for the BR64 antibody of the invention include its conjugation or linkage, e.g., by recombinant DNA techniques, to an enzyme capable of converting a prodrug into a cytotoxic drug and the use of that antibody-enzyme conjugate in combination with the prodrug to convert the prodrug to a cytotoxic agent at the tumor site [see, e.g., P. Senter et al., "Anti-Tumor Effects of Antibody-Alkaline Phosphatase Conjugates in Combination with Etoposide Phosphate", *Proc. Natl. Acad. Sci USA,* 85, pp. 4842–4846 (1988)]. Still another therapeutic use for the BR64 antibody involves its use, either in the presence of complement or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient [see, e.g., N. K. C. Ramsay et al., "Bone Marrow Purging Using Monoclonal Antibodies", *J. Clin. Immunol.*, 8 (No. 2), pp. 81-88 (1988)].

Furthermore, chimeric or other recombinant BR64 antibodies of the invention, as described earlier, may be used therapeutically. For example, a fusion protein comprising at least the antigen-binding region of the BR64 antibody joined to at least a functionally active portion of a second protein having anti-tumor activity, e.g., a lymphokine or oncostatin, may be used to treat human carcinoma in vivo. In addition, a chimeric BR64 antibody wherein the antigen-binding region of BR64 is joined to a human Fc region, e.g., IgG1, may be used to promote antibody-dependent cellular cytotoxicity or complement-mediated cytotoxicity. Furthermore, recombinant techniques known in the art can be used to construct bispecific antibodies wherein one of the binding specificities of the antibody is that of BR64 [see, e.g., U.S. Pat. No. 4,474,893].

In addition, other variants of the BR64 antibody, such as class-switch variants, may be used therapeutically. For example, the IgG2a variant, BR64.60, disclosed herein can promote ADCC and CDC by virtue of its particular subclass.

Finally, anti-idiotypic antibodies of the BR64 antibody may be used therapeutically in active tumor immunization and tumor therapy [see, e.g., K. E. Hellstrom et al., "Immunological Approaches to Tumor Therapy: Monoclonal Antibodies, Tumor Vaccines, and Anti-Idiotypes", in *Covalently Modified Antigens and Antibodies in Diagnosis and Therapy*, supra at pp. 35-41].

It is apparent therefore that the present invention encompasses pharmaceutical compositions, combinations, and methods for treating human carcinomas. For example, the invention includes pharmaceutical compositions for use in the treatment of human carcinomas comprising a pharmaceutically effective amount of a BR64 antibody and a pharmaceutically acceptable carrier. The compositions may contain the BR64 antibody, either unmodified, conjugated to a therapeutic agent (e.g., drug, toxin, enzyme or second antibody) or in a recombinant (e.g., chimeric or bispecific BR64) or variant form. The compositions may additionally include other antibodies or conjugates for treating carcinomas (e.g., an antibody cocktail).

The antibody compositions of the invention can be administered using conventional modes of administration, including, but not limited to, intravenous, intraperitoneal, oral, intralymphatic or administration directly into the tumor. Intravenous administration is preferred.

The antibody compositions of the invention may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The antibody compositions also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment, and the judgment of the treating physician. Accordingly, the dosages of the compositions should be titrated to the individual patient. Nevertheless, an effective dose of the antibody compositions of this invention may be in the range of from about 1 to about 2,000 mg/m$^2$.

In order that the invention described herein may be more fully understood, the following examples are set forth. It should be understood that these examples are for illustrative purposes only and are not to be construed as limiting the scope of this invention in any manner.

EXAMPLE 1

Preparation Of The BR64 Monoclonal Antibody

The BR64 monoclonal antibody of the invention was produced using hybridoma fusion techniques as described previously by M. Yeh et al., *Proc. Natl. Acad. Sci. USA*, (1979), supra, and M. Yeh et al., *Int. J. Cancer* (1982), supra. Briefly, a three month-old BALB/c mouse was immunized using as the immunogen explanted cultured cells from a human breast carcinoma, designated 3396 or H3396. The mouse received injections on four occasions: on the first three occasions, the mouse received 1 intraperitoneal injection and 1 subcutaneous injection split between 4 sites on the mouse. On the fourth occasion, the mouse was given only 1 intraperitoneal injection. The total number of cells injected on each occasion was approximately 10$^7$ cells. Three days after the last immunization, the spleen was removed and spleen cells were suspended in NS-1 culture medium. The spleen cells were then fused with NS-1 mouse myeloma cells in the presence of polyethylene glycol (PEG) and the cell suspension grown in microtiter wells in selective HAT medium as described by M. Yeh et al., supra [see, also, G. Kohler and C. Milstein, *Nature*, 256, pp. 495-497 (1975), and *Eur. J. Immunol.*, 6, pp. 511-519 (1976)]. The mixture was seeded to form low density cultures originating from single fused cells or clones.

The supernatants from these hybridoma cultures were then screened for direct binding activity on the breast cancer cell line, 3396, and a fibroblast cell line, using an ELISA assay similar to that described by J. Y. Douillard et al., "Enzyme-Linked Immunosorbent Assay for Screening Monoclonal Antibody Production Using Enzyme-Labeled Second Antibody", *Meth. Enzymol.*, 92, pp. 168-174 (1983).

According to this assay, the antigen (with which the antibody being screened for is reactive) is immobilized on microtiter plates and then incubated with hybridoma supernatants. If a supernatant contains the desired antibody, the antibody will bind to the immobilized antigen and is detected by addition of an anti-immunoglobulin antibody-enzyme conjugate and a substrate for the enzyme which leads to a measurable change in optical density. In the present studies, breast cancer cells or control fibroblast cells were dispensed into a 96-well tissue culture plate (Costar Cambridge, Mass.) and incubated overnight in a humid 37° C. incubator (5% CO$_2$). The cells were then fixed with 100 μl of freshly prepared 1.0% glutaraldehyde to a final well concentration of 0.5% and incubated for 15 min at room temperature, followed by washing three times with 1×PBS. The cells were next blocked for 30 min with 5% BSA in PBS and washed again three times with PBS. The supernatants from the hybridoma cultures were then added at 100 μl/well, the wells incubated for 1 h at room temperature, and the cells washed three times with PBS. Next, goat anti-mouse horseradish peroxidase (Zymed, Calif.) diluted in 0.1% BSA and PBS was added to a concentration of 100 μl/well. The reaction mixture was incubated for either 1 h at room temperature or 30 min at 37° C. and the cells were then washed three times with PBS. o-phenylenediamine (OPD) was then added at 100 μl/well and the plates incubated in the dark at room temperature for 5-45 min. Antibody binding to the cells was detected by a color change in the wells that occurred within 10-20 min. The reaction was stopped by adding 100 μl/well H and the absorbance read in a Dynatech (Alexandria, Va.) Microelisa autoreader at 490 nm.

It should be noted that this assay can be performed using intact cells or purified soluble antigen or cellular extracts as the immobilized antigen. When soluble antigen or cell extracts were used as antigen, the antigen was initially plated at 50 μl/well in PBS and the plates were incubated overnight at room temperature before beginning the assay. When using intact cells as antigen, they may be used fresh or after fixation. In either case, the cells were initially placed at $10^4$ cells at 100 μl/well in culture medium and incubated overnight in a 37° C. incubator (5% $CO_2$).

Hybridomas which produced antibodies binding to the breast cancer cell line and not to the fibroblast line were thus selected, cloned, expanded in vitro, and further tested for antibody specificity. Those hybridomas producing antibody reactive with human breast cancer were recloned, expanded, and injected into pristane-primed 3-month old BALB/c mice, where they grew as ascites tumors.

Following this procedure, hybridoma cell line BR64 was obtained, cloned, and injected into mice to develop as an ascites tumor. As disclosed above, the BR64 hybridoma has been deposited with the ATCC. Antibody secreted into the ascites was purified on protein A-Sepharose [see, e.g., P. L. Ey et al., *Immunochemistry*, 15, pp. 429-436 (1978)] or by gel filtration on Sephacryl S-300. Purified BR64 antibody was used for further characterization.

EXAMPLE 2

Characterization Of The BR64 Monoclonal Antibody

Isotype Determination

To determine the class of immunoglobulin produced by the BR64 hybridoma, the following techniques were utilized:

(a) Ouchterlony Immunodiffusion

An aliquot of supernatant of the hybridoma cells was placed into the center well of a 25% agar plate. Monospecific rabbit anti-mouse Ig isotype antibodies (Southern Biotechnology, Birmingham, Ala.) were placed in the outer wells and the plate was incubated for 24-48 h at room temperature. Precipitation lines were then read.

(b) ELISA Isotyping

Dynatech Immunolon 96-well plates were coated with goat anti-mouse Ig antibodies at 1 μg/ml concentration, 50 μl/well in PBS and left covered overnight at 4° C. The plates were washed with PBS/Tween 20, 0.05%, and blocked with medium at 100 μl/well for 1 h at room temperature. After washing the plates, supernatants from the BR64 hybridoma were added and incubated at room temperature for 1 h. After washing with PBS containing 2% bovine serum albumin (BSA), plates were incubated at 37° C. for 30 min with monospecific rabbit anti-mouse Ig isotype antibodies coupled to peroxidase (Zymed). After further washing, the plates were incubated with 1 mg/ml o-phenylenediamine and 0.03% $H_2O_2$ in 0.1M citrate buffer, pH 4.5. Optical density at 630 nm was determined on a Dynatec ELISA plate reader.

Based on these procedures, it was determined that the BR64 monoclonal antibody is of the IgG1 isotype.

Binding Characteristics Of The BR64 Monoclonal Antibody

Our experiments have shown that the BR64 antibody binds with a high degree of selectivity to a wide range of human carcinomas showing only a low degree of reactivity with certain normal cells. These experiments involved immunohistological studies on frozen tissue sections as well as binding studies using intact cultured cells.

The PAP technique of L. A. Sternberger, as described in *Immunochemistry*, pp. 104-169 (John Wiley & Sons, New York 1979), and as modified by H. J. Garrigues et al., "Detection of a Human Melanoma-Associated Antigen, p. 97, In Histological Sections of Primary Human Melanoma", *Int. J. Cancer*, 29, pp. 511-515 (1982), was used for the immunohistological studies. The target tissues for these tests were obtained at surgery and frozen within 4 h of removal using isopentane precooled in liquid nitrogen. Tissues were then stored in liquid nitrogen or at −70° C. until used. Frozen sections were prepared, air-dried, treated with acetone, and dried again [see H. J. Garrigues et al., supra]. Sections to be used for histologic evaluation were stained with hematoxylin. To decrease non-specific backgrounds, sections were preincubated with normal human serum diluted 1/5 in PBS [see H. J. Garrigues et al., supra]. Mouse antibodies, rabbit anti-mouse IgG, and mouse PAP were diluted in a solution of 10% normal human serum and 3% rabbit serum. Rabbit anti-mouse IgG (Sternberger-Meyer Immunochemicals, Inc., Jarettsville, Md.) was used at a dilution of 1/50. Mouse peroxidase-antiperoxidase complexes (PAP, Sternberger-Meyer Immunochemicals, Inc.) containing 2 mg/ml of specifically purified PAP was used at a dilution of 1/80.

The staining procedure consisted of treating serial sections with either specific antibody, i.e., BR64, or a control antibody for 2.5 h, incubating the sections for 30 min at room temperature with rabbit anti-mouse IgG diluted 1/50 and then exposing the sections to mouse PAP complexes diluted 1/80 for 30 min at room temperature. After each treatment with antibody, the slides were washed twice in PBS.

The immunohistochemical reaction was developed by adding freshly prepared 0.5% 3,3'-diaminobenzidine tetrahydrochloride (Sigma, St. Louis, MO) and 0.01% $H_2O_2$ in 0.05M Tris buffer, pH 7.6, for 8 min [see I. Hellstrom et al., *J. Immunol.*, 127, pp. 157-160 (1981)]. Further exposure to a 1% $OsO_4$ solution in distilled water for 20 min intensified the stain. The sections were rinsed with water, dehydrated in alcohol, cleared in xylene, and mounted on slides. Parallel sections were stained with hematoxylin.

The slides were each evaluated under code and coded samples were checked by an independent investigator. Typical slides were photographed by using differential interference contrast optics (Zeiss-Nomarski). The degree of antibody staining was evaluated as 0 (no reactivity), + (a few weakly positive cells), + + (at least one third of the cells positive), + + + (most cells positive), and + + + + (approximately all cells strongly positive). Because differences between + and O staining were less clear cut than between + and + + staining, a staining graded as + + or greater was considered "positive". Both neoplastic and stroma cells were observed in tumor samples. The staining recorded is that of the tumor cells because the stroma cells were not stained at all or were stained much more weakly than the tumor cells.

Table I below demonstrates the immunohistological staining of various tumor and normal tissue specimens using the BR64 monoclonal antibody. As the table clearly demonstrates, the BR64 antibody reacts with a wide range of human carcinoma specimens, does not react with non-carcinoma tumors such as melanoma and sarcoma, and shows no reactivity with a large number of normal human tissues tested. Additionally, our immunohistological studies have demonstrated that these carcinoma cells are strongly stained by the BR64 antibody. The antibody did show a weak binding to occasional cells in the testis and tonsils, and a reactivity with epithelial cells of the stomach and oesophagus and acinar cells of the pancreas. The table additionally indicates that, while studies by the inventors showed no reactivity of the antibody with normal heart tissue, independent testing at the NIH showed some reactivity with capillaries of the heart in certain normal donors.

TABLE I

IMMUNOPEROXIDASE STAINING OF HUMAN TUMORS AND NORMAL TISSUE SPECIMENS WITH BR64 MONOCLONAL ANTIBODY

| TISSUE TYPE | NUMBER POSITIVE/ NUMBER TESTED |
|---|---|
| Tumors | |
| Lung carcinoma (non-small cell) | 7/10 |
| Breast carcinoma | 9/13 |
| Colon carcinoma | 12/14 |
| Ovary carcinoma | 1/2 |
| Endometrial carcinoma | 3/3 |
| Stomach carcinoma | 3/3 |
| Pancreatic carcinoma | 2/2 |
| Oesophagus carcinoma | 3/3 |
| Cervical carcinoma | 1/1 |
| Melanoma | 0/8 |
| Sarcoma | 0/5 |
| Normal Tissues | |
| Lung | 0/4 |
| Spleen | 0/4 |
| Breast | 0/4 |
| Colon | 0/3 |
| Kidney | 0/5 |
| Liver | 0/4 |
| Brain | 0/2 |
| Heart* | 0/3 |
| Skin | 0/4 |
| Thyroid | 0/1 |
| Adrenal | 0/1 |
| Ovary | 0/2 |
| Lymph nodes | 0/2 |
| Uterus | 0/7 |
| Retina | 0/1 |
| Tonsil** | 2/2 |
| Testis** | 2/2 |
| Pancreas§ | 5/5 |
| Stomach§§ | 2/2 |
| Oesophagus§§§ | 2/2 |

TABLE I-continued

IMMUNOPEROXIDASE STAINING OF HUMAN TUMORS AND NORMAL TISSUE SPECIMENS WITH BR64 MONOCLONAL ANTIBODY

| TISSUE TYPE | NUMBER POSITIVE/ NUMBER TESTED |
|---|---|
| Lymphocyte pellet | 0/4 |

*Independent testing at NIH showed that capillaries in three of six samples of heart stained with BR64.
**Small population of the cells was positive.
§ Acinar cells positive.
§§ Epithelial cells positive.
§§§ Surface epithelial cells positive; basal cells negative.

Next, we studied the binding of the BR64 antibody to various cultured cell lines. Antibody binding to the cell surface of intact cultured cells was identified either by a direct binding assay with $^{125}$I-labeled antibody as described in J. P. Brown et al., "Quantitative Analysis of Melanoma-Associated Antigen p.97 In Normal And Neoplastic issues", Proc. Natl. Acad. Sci. USA, 78, pp. 539–543 (1981) or by direct immunofluorescence using a fluorescence activated cell sorter (FACS) II.

For the binding assays performed using radiolabeled antibody, various cultured cell lines were trypsinized to give a cell suspension and $1 \times 10^6$ cells were incubated on ice for 30 min with 10 hu 6 cpm of $^{125}$I-labeled antibody in 100 μl of binding buffer (15% FCS in IMDM). The suspension was layered onto 0.2 ml dinonylphthalate:dibutylphtalate (1:1 v/v) and centrifuged. The pellet and the aqueous phase were counted for $^{125}$I. To measure nonspecific binding, parallel incubations were performed with unlabeled antibody as a competitor.

For binding analyses using a FACS cell sorter, $1 \times 10^6$ cultured cells were aliquoted in 15% fetal bovine serum (FBS) in IMDM media (Gibco, N.Y.) to a total volume of 500 μl/tube. The cells were centrifuged for 1.5 min on a Serofuge and the supernatant removed. 100 μl of the BR64 monoclonal antibody at 10 μg/ml was added to each tube, the contents of which was then mixed and incubated on ice for 30 min. The reaction mixture was washed three times with 500 μl of 15% FBS/IMDM by centrifugation for 1.5 min on the Serofuge (tubes were blotted after the third wash). Then, 50 μl of optimized FITC-conjugated goat anti-mouse IgG antibody (Tago, Burlingame, Calif.) diluted 1:25 in 15% FBS/IMDM was added to each tube and the reaction mixture was mixed and incubated for 30 min. The wash step was then repeated and after blotting of the tubes, each pellet was resuspended in 200–500 μl of PBS. Each sample was run on a Coulter Epics C FACS and the mean fluorescence intensity (MFI) was determined. From the MFI, the linear fluorescent equivalent (LFE) was determined. The LFE of each test sample divided by the LFE of a negative control gave a ratio between the brightness of cells stained by specific vs. control antibody. The binding data is shown in Table II below (see also FIG. 10).

TABLE II

| Cell Line | Ratio |
|---|---|
| Breast carcinoma 3396 | 49 |
| Lung carcinoma 2707 | 13 |
| Colon carcinoma CB5 | 10 |
| Colon carcinoma RCA | 6 |
| Colon carcinoma C | 11 |
| T cell lymphoma CEM | 1 |
| T cell lymphoma MOLT-4 | 1 |
| B cell lymphoma P3HR-1 | 1 |

TABLE II-continued

| Cell Line | Ratio |
|---|---|
| Peripheral blood leukocytes | 1 |

As Table II and FIG. 10 demonstrate, the BR64 monoclonal antibody reacted with human breast, lung, and colon carcinoma cell lines but did not react with T or B lymphoma lines nor with normal peripheral blood leukocytes. BR64 also did not react with bone marrow stem cells (data not shown). Scatchard analysis using radiolabeled antibody indicated that the BR64 antibody has an approximate association constant (Ka) of $10^6 M^{-1}$ and that the carcinoma cell line 3396 has $0.5-1.0 \times 10^6$ antigen sites per cells.

EXAMPLE 3

Internalization Of The BR64 Monoclonal Antibody Within Carcinoma Cells

Studies were conducted to measure internalization of the BR64 monoclonal antibody within carcinoma cells. According to one procedure, BR64 was conjugated to the ricin A chain toxin to form an immunotoxin, BR64-RA, whose internalization by carcinoma cells was then determined.

Conjugation of the antibody to the toxin was carried out as follows: Deglycosylated ricin-A chain (Inland Labs, Austin, Tex.) [see, also, D. C. Blakey et al., *Cancer Res.*, 47, pp. 947-952 (1987)] was treated with dithiothreitol (5 mM) prior to gel filtration on G-25 Sephadex using PBS, pH 7.2 as eluant. This was added in a 2:1 molar ratio to the antibody in PBS, the antibody having been previously modified with N-succinimidyl-3-(2-pyridyldithio) propionate (SPDP) (Pierce, Rockford, Ill.) according to the procedure of J. M. Lambert et al., *J. Biol. Chem.*, 260, pp. 12035-12041 (1985). Reaction was allowed to ensue for 12-24 h at room temperature, and the solution was then diluted with 1 volume of $H_2O$. Removal of unconjugated antibody was achieved using Blue Sepharose CL-6B (Pharmacia, Uppsala, Sweden) [see P. P. Knowles et al., *Anal. Biochem.*, 160, pp. 440-443 (1987)]. The conjugate and excess ricin-A chain were eluted with high salt (10× PBS) and subjected to further purification on Sephacryl-300 (Pharmacia) using PBS as eluant. The resulting conjugate was free of unbound monoclonal antibody or ricin A-chain and consisted mostly of 1:1 adducts.

The internalization of BR64-RA by various carcinoma cell lines was then measured using a thymidine uptake inhibition assay. According to this assay, the inhibition of $^3H$-thymidine incorporation into the DNA of the carcinoma cells (i.e., the inhibition of cell proliferation) is a measure of the cytotoxic effect of BR64-RA on the cells and thus a measure of the internalization of the immunotoxin within the cell.

Carcinoma cells were plated into a 96-well microtiter plate at $1 \times 10^4$ cells/well in 150 µl of IMDM medium with 10% fetal calf serum (FCS). The BR64-RA immunotoxin (50 µl) was then added in log 10 serial dilutions, starting at 10 µg/ml final concentration down to 0.01 µg/ml. The reaction mixture was incubated for 6 h at 37° C. in a 5% $CO_2$ incubator. At this point, 50 µl of $^3H$-thymidine was added at 1 µCi/well, and the plate incubated for 6 h at 37° C. in a 5% $CO_2$ incubator. The assay plate was then frozen at −70° C. for at least 1 h and thawed in a gel dryer for 15 min. The cells were harvested onto glass fiber filters (Filter Strips, No. 240-1, Cambridge Technology) in plastic scintillation vials using a PHD cell harvester. 3 ml of scintillation counting liquid was added to the vials and the vials were counted on a Beckman LS3891 beta scintillation counter at 1 minute per sample.

The results of this assay were expressed as a percentage of the $^3H$-thymidine incorporated by untreated control cells. Graphs of the percent inhibition of thymidine incorporation vs. immunotoxin concentration for each cell line tested were plotted and are shown in FIGS. 1-6. In each assay, a non-internalizing immunotoxin control, L6-RA or P1.17-RA, in turn. L6 is an antibody that reacts with carcinoma cells but does not internalize. P1.17 is a non-internalizing IgG2a mouse myeloma protein that does not bind to any human cells and is available from the ATCC.

FIG. 1 depicts the percent inhibition of thymidine incorporation by cells from the H2707 lung carcinoma cell line caused by internalization of BR64-RA. Similar results were obtained with the H3396 breast carcinoma cell line, C colon carcinoma cell line, and RCA colon carcinoma cell line (see FIGS. 2-4). Thus, the BR64 antibody was internalized by these carcinoma cells. In contrast, BR64-RA was not internalized by the JiJoye cell line, a human B lymphoma cell line or by normal human fibroblasts (see FIGS. 5 and 6). This study therefore demonstrated not only internalization of the BR64 antibody but the selectivity of the internalization, i.e., for carcinoma cells A second internalization study measured the uptake of the BR64 monoclonal antibody by the breast carcinoma cell line 3396, using radiolabeled BR64.

The antibody was radiolabeled as follows: 20-40 µg of antibody was incubated with 1 mCi of Na $^{125}I$ (Amersham) and 10 µg of chloramine-T in 400-500 µl PBS for 2 min at approximately 4° C. The reaction was stopped by the addition of 10 µg of sodium metabisulfite and the labeled antibody purified by gel filtration on a Sephadex G-25 (superfine) column pretreated with approximately 1 ml of 2% BS and equilibrated with PBS. The specific activity of the $^{125}I$-BR64 was approximately $5.4 \times 10^6$ cpm/µg. The antibody was diluted with an equal volume of 2% BSA in PBS and aliquots were frozen at −70° C. [see, e.g., M. Yeh et al., *J. Immunol.*, 126 (No. 4), pp. 1312-1317 (1981), and J. P. Brown et al., *Proc. Natl. Acad. Sci. USA* (1981), supra].

$^{125}I$-BR64 was then used to measure internalization of the antibody as follows: Tumor cells from the breast cancer line 3396 ($2 \times 10^6$/35 mm dish) were cultured overnight in IMDM media containing 15% fetal calf serum (FCS). The cells were pre-cooled with cold (4° C.) PBS for 5 min and then incubated with the $^{125}I$-BR64 (107 cpm) at 4° C. for 30 min on a rocker platform. Unbound antibody was removed by extensive washing (7×6 ml) with culture media at 4° C. The cells were transferred to a 37° C. incubator and cultured for certain designated "chase" times. At the end of each chase period, the culture media was collected and counted in a gamma counter. This was designated the "media" fraction and represented monoclonal antibody released by the cells. The cell monolayer was then washed twice with PBS (5 ml each) and incubated with 0.1M acetic acid at 4° C. for 20 min (at t=0 time point only) or with trypsin (0.35%) at 37° C. for 10 min. The acetic acid-released material was counted as above and represented cell "surface" bound antibody at t=0. The trypsinized cells were collected and added to 1 ml of FCS. The cells were then centrifuged at 400 g for 4 min at 4° C. and the supernatant collected as cell "surface" antibody. The pellet was resuspended in 10 ml of culture media at 4° C. and washed twice by centrifugation. The final pellet was solubilized in an SDS containing buffer [RIPA=10 mM Tris, pH 7.2, 150 mM NaCl, 1% deoxycholate, 1% Triton X-100, 0.1% SDS, 1% aprotinin] and counted as above. This fraction represented "intracellular" monoclonal antibody. The cells which were treated with acetic acid were scraped and solubilized using the same SDS buffer and represented "intracellular" antibody at t=0.

The results of this study were as follows: The breast carcinoma 3396 cells grew as well-defined islands and at $2 \times 10^6$ cells/dish were nearly confluent. Incubation at 4° C. had no effect on cell morphology or cell adhesion. Antibody bound to the cell surface was eluted either with cold 50 mM acetic acid (4° C.) at t=0 or with trypsin (0.35 gm/100 μl) at t=2 min −6 h. The elution with trypsin required an incubation of 10 min at 37° C., and during this time, antibody was found to internalize, such that, at t=0, cells harvested with trypsin had approximately 50,000 cpm associated with the intracellular pool (data not shown) while the same pool for the acetic acid-eluted cells at 4° C. had only 12,000 cpm (see FIG. 7). In compiling the graphs shown in FIGS. 7 the 10 minute trypsinization period, i.e., a 2 minute chase time actually represents 2 minutes of chase +10 minutes trypsin incubation.

The cells incorporated >70,000 cpm/dish during the 30 min pulse with $^{125}$I-BR64 at 4° C. At t=0, 80% of the monoclonal antibody was released with 50 mM acetic acid (4° C.), i.e., was found on the cell surface. Our data however (as depicted in FIGS. 7 and 8), shows that the BR64 monoclonal antibody associated with the cell surface decreased rapidly with a reciprocal increase in the intracellular pool when the cells were incubated at 37° C.

Figure 7:
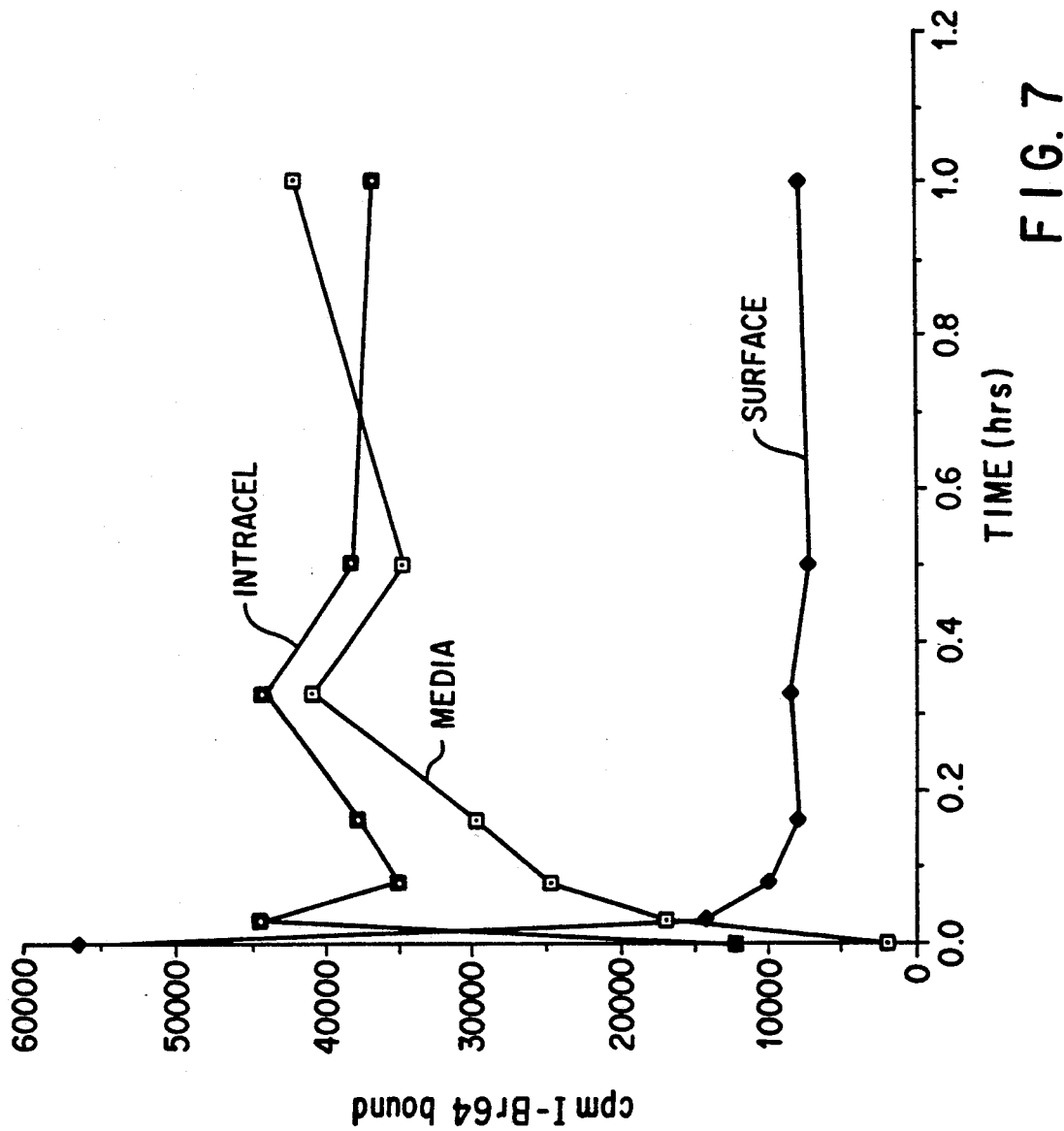
FIG. 7 depicts the uptakes of $^{125}$I-labeled BR64 antibody by breast carcinoma cells within one hour after a pulse-chase experiment. Measurements were taken of labeled antibody in the cell media:      , on the cell surface:       , and within the cell (intracellular)
Figure 8:
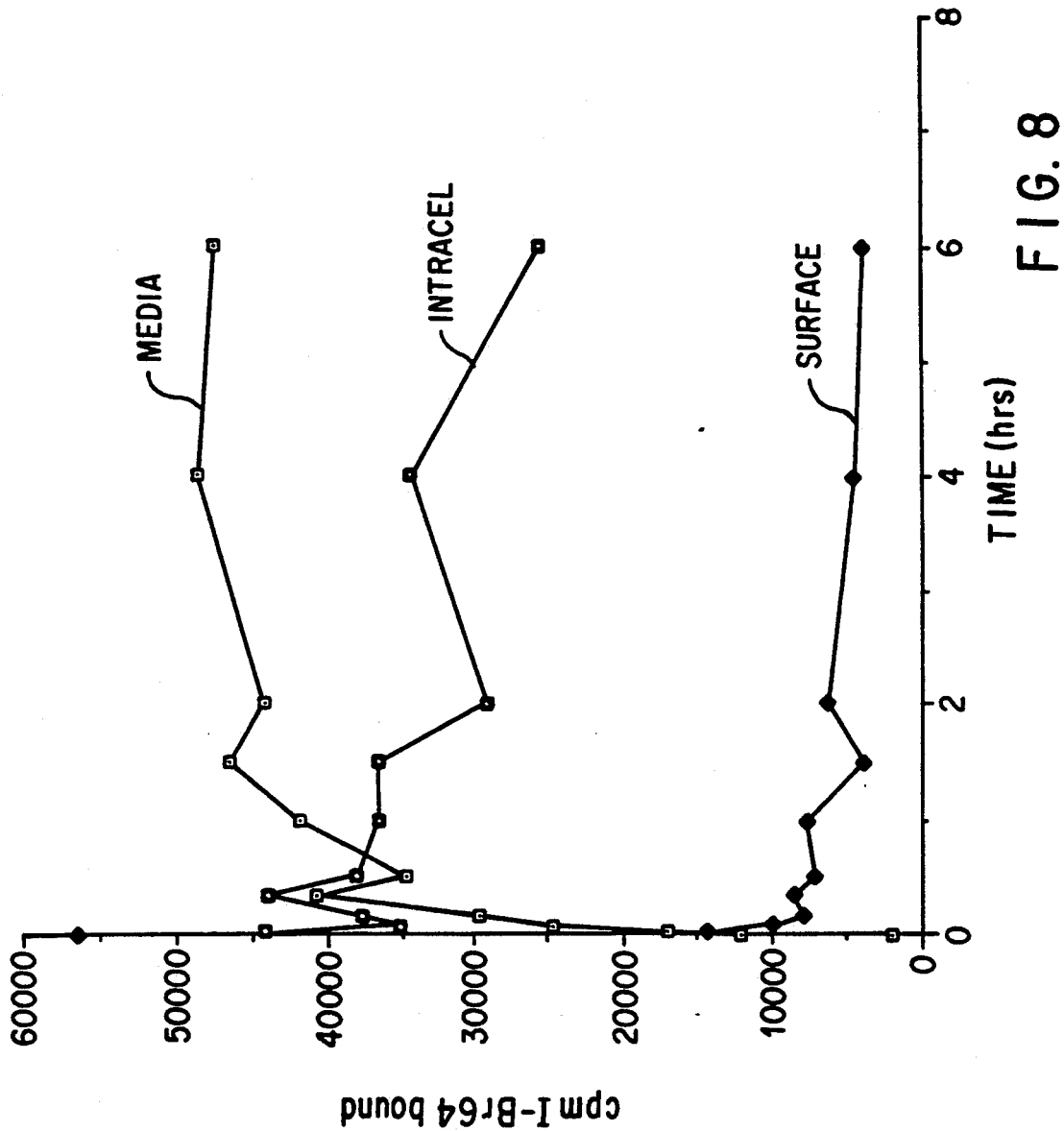
FIG. 8 depicts the uptake of $^{125}$I-labeled BR64 antibody by breast carcinoma cells within six hours after a pulse-chase experiment. Measurements were taken of labeled antibody in the cell media:      , on the cell surface:       , and within the cell (intracellular)

As demonstrated in FIG. 7, by 2 minutes of chase, 60% of the BR64 antibody was intracellular while 20% was released into the media. The cell surface antibody reached a steady state of approximately 10% of the total cell-associated radioactivity. As shown in FIGS. 7 and 8, at 1 hour of chase, the amount of antibody found in the intracellular pool and the amount of antibody released into the media were roughly equivalent, i.e., 45% of radiolabel. Finally, as depicted in FIG. 8, after 1 hour of chase, the amount of labeled antibody in the intracellular pool slowly decreased such that by 6 hours, 32% of the radiolabel was found in this compartment, while the media now contained 60%.

This internalization study therefore shows that BR64 is rapidly internalized within the carcinoma cells. Over time, the majority of the antibody is released into the culture media; however, there is a significant proportion associated with the intracellular compartment even after 6 hours. As discussed earlier, the ability of the BR64 antibody of this invention to be internalized within the carcinoma cells with which it reacts makes the antibody particularly useful for therapeutic applications for the treatment of human carcinomas.

EXAMPLE 4

In Vitro Cytotoxic Activity Of A BR64-Adriamycin Conjugate On Carcinoma Cells

The present example further illustrates the therapeutic potential of the BR64 antibody in the form of an antibody-drug conjugate for the effective killing of carcinoma cells. According to the experiments described herein, a BR64-adriamycin conjugate showed a significant cytotoxic effect on carcinoma cells in vitro.

The BR64-adriamycin (ADR) conjugate was constructed as follows: ADR was derivatized with cis-aconitic anhydride using a method previously reported for the derivatization of daunomycin [see W. C. Shen et al., *Biochim. Biophys. Res. Commun.*, 102, pp. 1048-1054 (1981)]. The lyophilized product was dissolved in PBS (2.4 mg/ml) and activated with 2 eq. of 1-ethyl-3-(3-dimethylamino propyl)carbodiimide (EDC) (Pierce, Rockford, Ill.). After 10 min at room temperature, the drug derivative was added to the BR64 antibody (5–10 mg/ml in PBS) in a 15:1 mole ratio and the reaction was allowed to proceed for 2-4 h. Gel filtration on G-25 Sephadex followed by treatment with polystyrene beads (SM-2 beads, Bio-Rad, Richmond, Calif.) and sterile filtration gave conjugates that were free of unconjugated drug. The BR64:ADR ratios ranged from 3.0–5.0. The chemistry employed was similar to previously reported methods [see, e.g., H. M. Yang et al., *Proc. Natl. Acad. Sci. USA*, 85, pp. 1189-1193 (1988)].

The BR64-ADR conjugate was then tested for its cytotoxic effect on H3396 carcinoma cells using a $^3$H-thymidine uptake assay wherein a suspension of $1 \times 10^4$ carcinoma cells in 150 μl of IMDM containing 10% FBS was added to each well of a 96-well mictotiter plate and allowed to adhere overnight at 37° C. Dilutions of the conjugate in IMDM+10% FBS were added and incubation at 37° C. was allowed to proceed for 4 h. The wells were washed twice and incubation was continued for 20 h with a pulse of $^3$H-thymidine (1 μCi/well) in the last 6 h. The plates were frozen at −20° C. to detach the cells and the cells were harvested onto glass fiber discs. The filters were counted on a Beckman 3701 scintillation counter.

Figure 9:
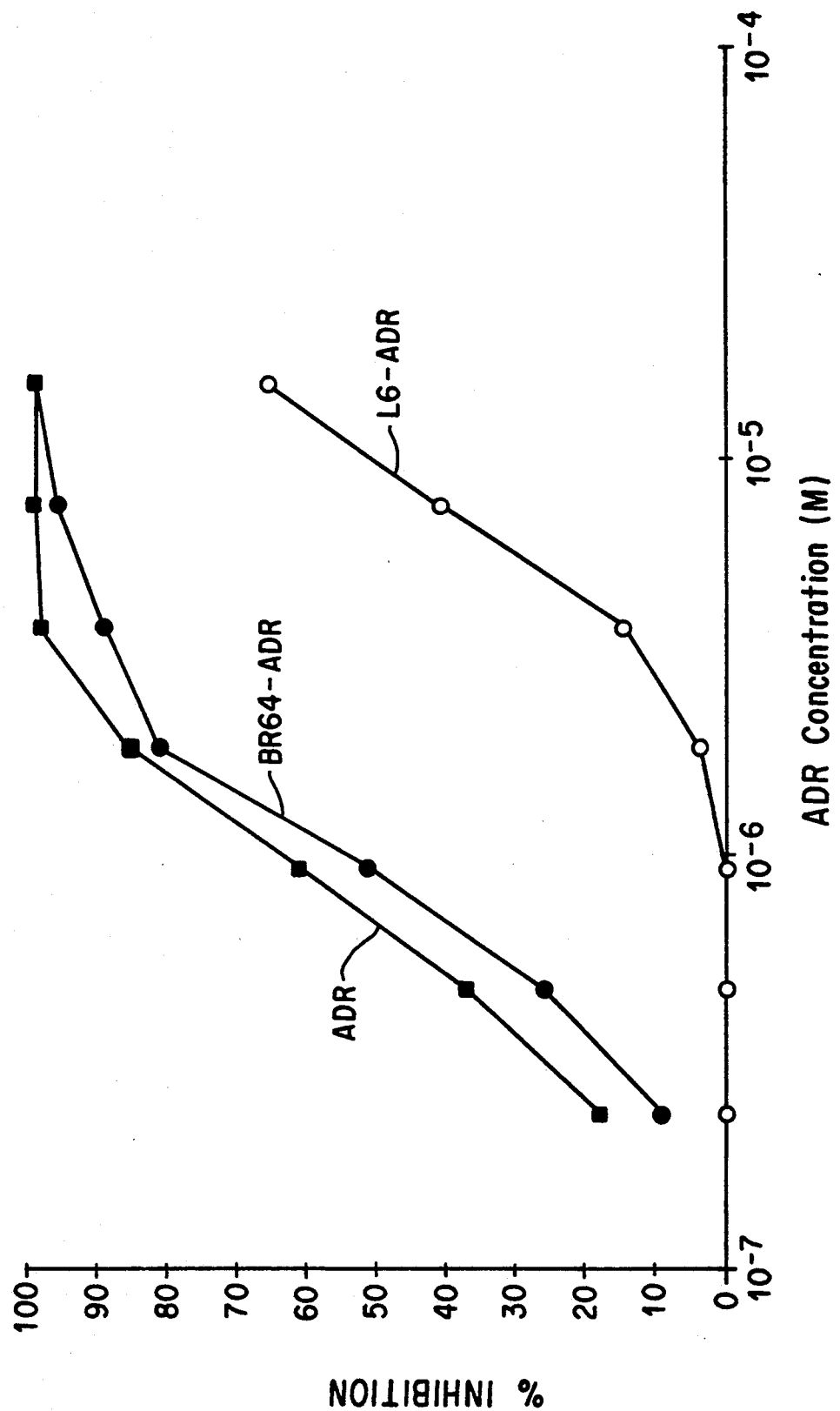
FIG. 9 depicts the percent inhibition of thymidine incorporation into the DNA of H3396 breast carcinoma cells treated with a BR64-adriamycin conjugate. A significant cytotoxic effect was demonstrated.

As depicted in FIG. 9, the BR64-ADR conjugate exhibited a significant cytotoxic effect on the carcinoma cells comparable to the effect observed with ADR alone. An L6-ADR conjugate was used as a negative control. In addition, the BR64-ADR conjugate did not display such killing on antigen-negative target cells (data not shown).

EXAMPLE 5

Characterization Of The BR64 Antigen

The BR64 antibody was tested for reactivity with a variety of immobilized purified glycolipids of known carbohydrate structures, using an ELISA assay in which the antigens and antibody were used in excess. The glycolipids were dried from methanol in microtiter wells at 100 ng/well. Purified antibody was assayed at a concentration of 10 μg/ml in 0.01M Tris-HCl, pH 7.4, containing 1% bovine serum albumin. Absorbance values were calculated as the average of duplicate wells.

As shown in FIG. 11, the BR64 antibody bound specifically to plated Le$^y$ and H2 antigens; H2 having the same structure as Le$y$(Fuc$\alpha$1-2Gal$\beta$1-4(Fuc$\alpha$1-3)GlcNAc) but lacking an internal Fuc$\alpha$1-3. Earlier immunoprecipitation studies with BR64, in which the BR64 antigen was solubilized and analyzed by SDS-PAGE, have indicated that the BR64 antigen is not a glycoprotein (data not shown). Thus, it appears that the BR64 antibody binds to a complex epitope on a novel, internalizing pan-carcinomic glycolipid antigen, a portion of that epitope comprising an Le$^y$ carbohydrate chain.

EXAMPLE 6

Preparation Of A Subclass-Switch Variant of BR64

In the present example, the subclass of the original BR64 antibody was switched from IgG1 to IgG2a.

Variants of the BR64 cell line (ATCC No. HB 9895) producing an altered heavy chain isotype were generated by a combination of sib selection and cloning in soft agarose. Microtiter plates were seeded with 1,000 cells/well of the parental BR64 cells and naturally-occurring subclass-switch variants were selected as described by G. Spira et al., supra.

Briefly, the BR64 cells in the wells were allowed to grow to near confluence in Iscoves Medium (Grand Island Biological Co., Grand Island, N.Y.) supplemented with 15% FCS and 2× glutamine. The medium has been filtered through a non-triton containing Millex filter (Millipore Corp., Bedford, Mass.) and kept out of fluorescent light.

After 7 days growth in the wells, the cells had reached near confluence and the supernatants from the wells were removed and assayed via an ELISA for the presence of an IgG2a immunoglobulin (see Spira et al., supra at p. 309). Positive wells were identified and quantitated using an automatic ELISA reader. The cells from each of the positive wells were replated into multiple wells of microtiter plates and allowed to grow for 7 days. The ELISA assay was repeated and cells from the most highly reactive wells were pooled.

Cells from these pools were then cloned in soft agarose containing an IgG2a specific antiserum [see G. Spira et al., supra at p. 310). Clones that formed an immunoprecipitate indicating the secretion of an IgG2a immunoglobulin were recovered and grown in mass culture. Culture supernatants were assayed for the presence of the parental IgG1 and all other mouse IgG isotypes. Clones that produced only the IgG2a isotype were then selected for antibody production. One such clone was BR64.60 as deposited with the ATCC.

EXAMPLE 7

The Cytotoxic Activity Of The BR64.60 Antibody

Determination of the ADCC activity of the BR64.60 monoclonal antibody was performed as described by Hellstrom et al., Proc. Natl. Acad. Sci. (USA), 82, pp. 1499-1502 (1985). Briefly, a short-term $^{51}$Cr-release test that measures the release of $^{51}$Cr as described by Cerrotini et al., Adv. Immunol., 18, pp. 67-132 (1974) was used as evidence of tumor-cell lysis, i.e., cytotoxicity. Peripheral blood lymphocytes from healthy human subjects were separated on LSM (Lymphocyte Separation Medium) (Organon Technica Div., Durham, N.C.) to provide effector cells equal to 5% natural killer cell reactivity against 2 different target cell lines, carcinoma cell lines 3655 and 3633 [see Hellstrom et al., Int. J. Cancer, 27, pp. 281-285 (1981)]. 106 target cells were labeled by incubation with 100 μCi (1 Ci=37 GBq) of $^{51}$Cr for 2 h at 37° C., after which they were washed 2 times and resuspended in IMDM medium plus 10% FCS. The labeled cells were seeded (2×10$^4$ cells per well in 67 μl) into Microtiter V-bottom plates (Dynatech Laboratories, Alexandria, Va.). Purified BR64.60 antibody (0.1 μg/ml-10 μg/ml) was then added, followed by 2×10$^6$ lymphocytes per well in 67 μl. The mixtures were incubated for 2 to 4 h after which the plates were centrifuged at 400× g. The supernatants were removed and the radioactivity in 100 μl samples was measured with a gamma-counter. There were 2 replicates per group; the variation between replicates was less than 10%.

Spontaneous release was defined as the counts per minute (cpm) released into the medium from target cells exposed to neither antibodies nor lymphocytes, and total release was defined as the number of counts released from target cells that were osmotically lysed at the end of the assay. Percent cytotoxicity was calculated as follows:

$$\frac{\text{experimental group release} - \text{spontaneous release}}{\text{total release} - \text{spontaneous release}} \times 100$$

Effector cells were characterized by assessing their sensitivity to incubation with anti-serum to the Leu-11b surface marker and guinea pig complement, using procedures described by Hellstrom et al., in Monoclonal Antibodies and Cancer Therapy, UCLA Symposia on Molecular and Cellular Biology, New Series, Reisfeld & Sell, (eds.), Liss, N.Y., 27, pp. 149-164 (1985). This was done to measure the expression of the Leu-11b marker, which characterizes natural killer (NK) cells and is expressed by lymphocytes mediating ADCC against human carcinoma cells in the presence of monoclonal antibody BR64.60.

The results shown in Table A indicate that BR64.60 mediates ADCC activity at concentrations of from 0.1-10 μg/ml antibody. This ADCC activity is seen when BR64.60 is tested on antigen-positive cell lines such as the lung and ovarian carcinoma cell lines used. The NK effector cells alone gave a background cytotoxicity ranging between 11-22% depending upon the particular cell lines used.

TABLE A

| | % Cytotoxicity | | | |
|---|---|---|---|---|
| | | BR64.60 Antibody Concentration μg/ml | | |
| Cell Line | NK | 10 | 1 | 0.1 |
| Lung ca. 3655 | 11 | 58 | 37 | 12 |
| Ovar. ca. 3633 | 22 | 68 | 44 | 30 |

Tests to evaluate the ability of monoclonal antibody BR64.60 to kill tumor cells in the presence of human serum as a source of complement, i.e., CDC activity, were performed similarly to those for the ADCC tests described above, except that 67 μl of human serum from normal human subjects as the source of complement diluted 1:3 to 1:6 was added per microtest well in place of a suspension of effector cells.

As shown in Table B below, BR64.60 gave a cytotoxic effect in the presence of human serum at concentrations of about 5-10 μg/ml antibody.

TABLE B

| | % Cytotoxicity | | | | |
|---|---|---|---|---|---|
| | BR64.60 Antibody Concentration μg/ml | | | | |
| Cell Line | 10 | 5 | 1 | 0.5 | 0.1 |
| Breast ca. | | | | | |
| 3680 | 100 | 84 | 14 | | 1 |
| 3396 | 100 | 90 | 14 | | 4 |
| MCF7 | 91 | 80 | 13 | | 0 |
| 3630 | 93 | 92 | | 4 | 2 |
| Ovar. ca. 3633 | 40 | 12 | 4 | | 1 |

TABLE B-continued

| | % Cytotoxicity | | | | |
| | BR64.60 | | | | |
| | Antibody Concentration | | | | |
| | µg/ml | | | | |
| Cell Line | 10 | 5 | 1 | 0.5 | 0.1 |
| --- | --- | --- | --- | --- | --- |
| Lung ca. 3655 | 35 | | 15 | | 2 |

While we have hereinbefore presented particular embodiments of this invention, it is apparent that variations and modifications can be effected within the scope of the invention. Therefore, it will be appreciated that the scope of this invention is to be defined by the claims appended hereto rather then by the specific embodiments which have been presented hereinbefore by way of example.

I claim:

1. Monoclonal antibody BR64 produced by the hybridoma having the identifying characteristics of HB 9895 as deposited with the ATCC.
2. Monoclonal antibody BR64 produced by the hybridoma having the identifying characteristics of HB 10292 as deposited with the ATCC.
3. An Fab, F(ab')$_2$ or Fv fragment of the monoclonal antibody of claim 1 or 2.
4. The monoclonal antibody of claim 1 or 2, wherein the antibody is conjugated to a label that produces a detectable signal.
5. The monoclonal antibody of claim 4, wherein the label is selected from the group consisting of a radiolabel, an enzyme, a chromophore or a fluorescer.
6. Hybridoma HB 9895 as deposited with the ATCC.
7. Hybridoma HB 10292 as deposited with the ATCC.
8. A class or subclass switch variant of the monoclonal antibody of claim 1.

* * * * *

UNITED STATES PATENT AND TRADEMARK OFFICE
CERTIFICATE OF CORRECTION

PATENT NO. : 5,242,824

DATED : September 7, 1993

INVENTOR(S) : Ingegerd Hellstrom and Karl E. Hellstrom

It is certified that error appears in the above-identified patent and that said Letters Patent is hereby corrected as shown below:

On the title page, item (56): Other Publications
    page 3, column 1, lines 1-2, delete "Novel Effector Functions' Nature, 312 pp. 604-608 (1984)."

page 3, column 2, last line, "Neuberger et al., 'Recombinant Antibodies Possessing" should read -- Neuberger, et al., "Recombinant Antibodies Possessing Novel Effector Functions," Nature, 312, pp. 604-608 (1984). --.

Claim 2, line 1, "BR64" should read -- BR64.60 --.

Signed and Sealed this

Twentieth Day of September, 1994

Attest:

BRUCE LEHMAN

*Attesting Officer*     *Commissioner of Patents and Trademarks*